US009563044B2

(12) United States Patent
Kosanic et al.

(10) Patent No.: US 9,563,044 B2
(45) Date of Patent: Feb. 7, 2017

(54) REFLECTIVE OPTICAL OBJECTIVE

(71) Applicant: ECOLE POLYTECHNIQUE FEDERALE DE LAUSANNE (EPFL), Lausanne (CH)

(72) Inventors: Davor Kosanic, Lausanne (CH); Bastien Rachet, Lausanne (CH); Victor Cadarso, Renens (CH); Juergen Brugger, Vufflens-La-Ville (CH)

(73) Assignee: ECOLE POLYTECHNIQUE FEDERALE DE LAUSANNE, Lausanne (CH)

( * ) Notice: Subject to any disclaimer, the term of this patent is extended or adjusted under 35 U.S.C. 154(b) by 0 days.

(21) Appl. No.: 14/415,106

(22) PCT Filed: Jul. 15, 2013

(86) PCT No.: PCT/IB2013/055806
§ 371 (c)(1),
(2) Date: Jan. 15, 2015

(87) PCT Pub. No.: WO2014/013412
PCT Pub. Date: Jan. 23, 2014

(65) Prior Publication Data
US 2015/0198793 A1    Jul. 16, 2015

(30) Foreign Application Priority Data

Jul. 17, 2012    (WO) .................. PCT/IB2012/053642

(51) Int. Cl.
*G02B 17/06*       (2006.01)
*A61B 1/00*        (2006.01)
(Continued)

(52) U.S. Cl.
CPC ............. *G02B 17/06* (2013.01); *A61B 1/0011* (2013.01); *A61B 1/00082* (2013.01);
(Continued)

(58) Field of Classification Search
CPC ..... G02B 17/06; G02B 3/0056; G02B 17/002; G02B 17/061; G02B 17/0808; G02B 17/086; G02B 21/04; G02B 23/243; A61B 1/00082; A61B 1/00096; A61B 1/0011; A61B 1/00165
(Continued)

(56) References Cited

U.S. PATENT DOCUMENTS 3,814,504 A    6/1974  Brady et al.

FOREIGN PATENT DOCUMENTS

DE          19729245 C1     5/1999
EP          0294902 A1      12/1988
WO          WO-99/03008 A1  1/1999

*Primary Examiner* — Bumsuk Won
*Assistant Examiner* — Wen Huang
(74) *Attorney, Agent, or Firm* — Choate, Hall & Stewart LLP; William R. Haulbrook

(57) ABSTRACT

The present invention relates to a reflective optical objective (1) comprising: —a first reflecting element (3) including a front surface (3a) and a hack surface (3b), the front surface (3a) including a convex reflecting surface (11); and —a second reflecting element (5) including a concave reflecting surface (13) facing the convex reflecting surface (11) of the first reflecting element (3), the second reflecting element (5) including a transmissive section (7) permitting electromagnetic radiation to pass through the concave reflecting surface (13) of the second reflecting element (5) to the first reflecting element (3). The reflective optical objective (1) is characterized in that the reflective optical objective (1) includes a carrier material (9) embedding at least the front surface (3a) of the first reflecting element (3) and defining the distance (d) between the first (3) and second (5) reflecting elements.

18 Claims, 13 Drawing Sheets

(51) Int. Cl.
  *G02B 17/00*   (2006.01)
  *G02B 17/08*   (2006.01)
  *G02B 3/00*    (2006.01)
  *G02B 21/04*   (2006.01)
  *G02B 23/24*   (2006.01)

(52) U.S. Cl.
  CPC ...... *A61B 1/00096* (2013.01); *A61B 1/00165* (2013.01); *G02B 3/0056* (2013.01); *G02B 17/002* (2013.01); *G02B 17/061* (2013.01); *G02B 17/086* (2013.01); *G02B 17/0808* (2013.01); *G02B 21/04* (2013.01); *G02B 23/243* (2013.01)

(58) Field of Classification Search
  USPC ....................................................... 359/850
  See application file for complete search history.

REFLECTIVE OPTICAL OBJECTIVE

TECHNICAL FIELD OF THE INVENTION

The present invention generally relates to optical systems for microscopy (in particular high-resolution microscopy) or microlithography, and more particularly relates to a reflective optical objective. The reflective optical objective operates in transmission meaning that it transfers electromagnetic radiation received on one side of the device through the device to the other side. A primary aimed application of the present invention is a parallel scanning confocal and multiphoton microscopy, with special emphasis on fluorescence microscopy for in-vivo applications.

The following description describes the reflective optical objective/optical device for microscopy imaging and a way of manufacturing such a device. This optical device is capable of producing high-resolution imaging can be appropriately adapted to many microscopy and microlithography procedures.

BACKGROUND OF THE INVENTION

High-resolution, scanning fluorescence microscopy methods, such as confocal microscopy or multi-photon microscopy, using standard refractive optics face the limitation of a trade-off between resolution and signal detection sensitivity on the one hand versus the image area (field of view) of the acquired image on the other.

Applications in the field of life sciences, histology and clinical tissue imaging using high-resolution fluorescence microscopy would largely benefit from overcoming this trade-off.

Imaging large surfaces of cell cultures, ex-vivo tissue samples and in-vivo tissue structure would enhance the efficiency of automatized imaging procedures in biology and histology and increase the quality of medical diagnosis based on histological imaging ex-vivo and in-vivo.

Overcoming the above mentioned trade-off and at the same time miniaturising the microscopy device would have a significant impact on endoscope based applications of microscopy imaging of internal organs in a non-invasive manner.

In the clinical environment, microscopic imaging by means of confocal scanning endomicroscopy inside the living patient is a recent trend in endoscopy. It has the potential to provide the physician with histological insights of the tissue, helping to discriminate healthy from potentially malignant or diseased tissue.

Confocal scanning endomicroscopy, similar to standard confocal microscopy, requires a fluorescent stain to produce image contrast by means of fluorescence excitation. Either endogenous autofluorescence or a fluorescent agent can be excited by means of laser light. Confocal scanning endomicroscopy has shown very promising results for cancer detection and tissue characterisation during on-going clinical procedures (Kiesslich et al, Atlas of Endomicroscopy, Springer 2008).

The two Endomicroscopy systems that are used in clinics today use fundamentally different technologies. Optiscan Imaging has developed a miniaturized MEMS based scanner that is integrated into the distal end of a specific endoscope, which is marketed as a complete system for gastroenterological endoscopy (Evans and Nishioka, Curr Opin Gastroenterol 2005; 21: 578-584). The Optiscan system uses small lenses to focus the light into the tissue of interest, which consequently results in a field of view which is significantly smaller than the device dimension.

On the other hand, Mauna Kea Technologies has developed a multi-core fiber based system that is scanned on the proximal end of the fiber bundle, where each fiber core serves as a pinhole (Thiberville et al., Proc Am Thorac Soc 2009, 6: 444-449). The imaging fiber is either used with a focusing lens at the distal tip or without any focusing optics. If no focusing optics is used, the ratio of device size to field of view can be increased at the expense of image resolution.

The size of the focusing optics has a significant impact on the application fields of endoscopy. For instance, Mauna Kea Technologies' system is a thin probe that can be inserted through the working channel of standard endoscopes, and thus be applied in different medical fields, such as gastroenterology, pulmonology or urology.

In this context, the present invention advantageously addresses the following points:
  Keeping high resolution while increasing the field of view;
  Improving the ratio of device dimension to field of view, close to one;
  Confocal imaging; and
  Increase of imaging depth in tissue.

Imaging large tissue areas with high resolution, while taking up less space in the tip of the endoscope, significantly increases the medical utility of endomicroscopy for performing live-histology (optical biopsy) of living tissue.

Increasing the imaging depth in order to reach the submucosal layer during an endomicroscopy procedure would open the possibility to perform accurate staging of early-stage tumours. Precise tumour staging is key in appropriate therapy choice and influences largely patient mortality and morbidity as well as the overall cost of the treatment.

Endomicroscopy is a novel medical field (Waldner et al, Nat Protoc 2011; 6(9): 1471-81, 2011 and citations therein), dating back to the early 2000's. Integrating a miniaturized fluorescence microscope into a medical endoscope provides the endoscopist with the possibility to see the cellular structure of the tissue under investigation, similar to conventional histology after biopsy extraction. Using confocal endomicroscopes and appropriate fluorescent dyes allows for image sectioning in the axial direction. This insight into the deeper layers of the tissue during ongoing procedures is important for a precise medical diagnosis of tissue disorders, such as early-stage tumors or pre-tumorous conditions (dysplasia f.i.).

A multitude of patents have been filed since the year 2000, either to protect the method of confocal endomicroscopy, the particular technological implementation of endomicroscopes or integration aspects into endoscopes, by the companies principally active in commercializing Endomicroscopy systems: Optiscan Imaging (Dabbs et al. 1990, WO9001716) in Marketing collaboration with Pentax Medical, and Mauna Kea Technologies (Viellerobe et al. 2001, WO2003056378).

In recent years, a new wave of prototypes for the next generation confocal scanning endomicroscopes (Jabbour et al., Ann Biomed Eng 2012; 40(2): 378-97, 2012 and citations therein) have been developed and patented or published. In parallel, much work has been done by different groups to develop non-linear scanning endomicroscopes (Wu & Li, Handbook of Photonics for Biomedical Science (Edited by V. V. Tuchin), CRC Press 2010, 547-74 and citations therein; Ben-Yakar et al. 2011, WO2011091283). Non-linear fluorescence imaging is technologically more sophisticated to implement into an endoscope, but offers the following advantages over confocal fluorescence imaging for in-vivo medical applications (Helmchen and Denk, Nat Methods 2005, 2(12): 932-40, 2005):

Inherent confocal sectioning due to non-linear fluorescence excitation;
Better collection of excited fluorescence, due to avoiding a pinhole;
Imaging deeper in the tissue, if near-infrared lasers are used for fluorescence excitation;
Possibility to excite second harmonic generation and image without external dyes inherent tissue features, such as collagen fibers; and
Less overall photo-damage at similar laser powers, due to fluorescence excitation confined to the focal spot.

The great majority of the published or patented endomicroscopy devices use small, single refractive elements for light focusing in the tissue of interest. Such refractive elements are typically small lenses or gradient-index lenses (GRIN). These elements suffer from stronger optical aberrations compared to standard, corrected microscope objectives. Furthermore, these elements are limited in the numerical aperture that they can reach. The numerical aperture defines the resolution of the image, the fluorescence collection efficiency and the efficiency of fluorescence excitation.

Webb and Xu proposed in 2009 (Webb et al. 2009, WO2009064746) a focusing system for a non-linear microscopy endoscope with two distinct regimes for the focusing of excitation light and the collection of fluorescence light. Using a dichroic layer on a lens—adapted to transmit the spectral range of the fluorescence light and to reflect the spectral range of the excitation light—the excitation light is focused on the basis of light reflection and the fluorescence light is collected on the basis of refraction with the same coated high numerical aperture lens. The advantage of Webb's and Xu's approach is the increased fluorescence excitation efficiency, due to excitation light focusing by means of a reflector. The arrangement of the reflective surfaces is very similar to the well-known design of a Schwarzschild microscope objective. Webb and Xu propose the usage of only one, macroscopic, such Schwarzschild-type element, resulting in a ratio between the image field-of-view and the overall device cross-section dimensions, far from the ratio of 1:1, and comparable to ratios of purely refractive systems.

In spite of a range of clinical benefits, current endomicroscopy systems are criticized by its end-users, the physicians, for several aspects. The subjects of the most recurrent criticisms are: increased overall procedure duration, long learning curve or the high price of equipment.

From the technological point of view, improvements of the image acquisition rate (reduction of motion artifacts), imaging of deeper tissue sections for better tumor staging or a larger image field of view while maintaining high contrast and resolution are requested, as summarized by Hwang (Hwang 2009) for applications the upper GI for instance.

The trade-off between the image area and image resolution/definition—is a known and barely resolved problem in microscopy. If a large image with high resolution is required, the obvious solution is to sequentially image small sample areas with high resolution. Reconstructing the image with mosaic stitching algorithms is the subsequent step.

However, this is highly time consuming and can additionally result in image artefacts. If scanning microscopy techniques such as confocal microscopy or multiphoton microscopy are considered, then the time consuming aspect becomes even more striking, since the scanning image acquisition is several factors slower than wide-field imaging.

To improve the performance of refractive elements, such as lenses, to stretch the above mentioned trade-off while remaining in typical scanning time frames, the most recent and significant was done by Amos et al. (Saini, Science 2012, 335(6076): 1562-3) who proposed a "mesolens".

This mesolens is a large lens that allows for confocal imaging of an entire embryo while maintaining resolution of single cells. However, in the case of the "mesolens" the overall dimensions of the microscope increase to several tens of centimeters, making it unsuitable for endomicroscopic applications. Optical aberrations have to be corrected with additional optical elements, which is valid for most optical systems that use refractive elements. Furthermore, using even such sophisticated lens systems as the mesolens, the maximal achieved image size remains in the order of a few millimeters.

In 2009 Rachet et al. (Rachet et al. 2009, WO2010084478) proposed a solution for overcoming this trade-off using an array of focusing micromirrors within a confocal scanning laser fluorescence microscope.

However, the microscopy device of WO2010084478 requires a thin ex-vivo sample preparation and is not suited for epi-fluorescence, forward-imaging of thick tissue in-vivo or living tissue of a patient in a clinical environment. Moreover, the collected light has to traverse the thin sample before the signal is detected by a camera or sensor.

Reflective microscope objectives are also known, however, these objectives are bulky and unsuitable for in-vivo imaging. Moreover, these objectives require a supporting structure for their optical reflectors that results in a loss of the optical signal transferred through the objective.

A goal of the present invention is to solve the above mentioned problems and in particular to provide an optical element permitting high resolution imaging of a large image area, increased imaging depth in tissue, that can be miniaturised for parallel imaging of large areas with high resolution and that also permits imaging of thick tissue in-vivo or living tissue of a patient in a clinical environment.

SUMMARY OF THE INVENTION

In view of the above, the present invention thus relates to a reflective optical objective according to claims 1 and 8.

Additionally, the invention concerns an array according to claim 9 comprising a plurality of reflective optical objectives, an optical element according to claim 10, an optical device according to claim 11, a microscope according to claim 12, an endoscope or endomicroscope according to claim 13, a catheter according to claim 13 and a method for producing a reflective optical objective according to claim 16.

Other features and advantages are found in the dependent claims.

The reflective optical objective (or micro-optical element) of the present invention is advantageously a miniaturised reflective objective (or reflective micro objective). An array of such elements allows for parallel imaging of large areas with high resolution.

The reflective optical objective is used with light, i.e. electromagnetic radiation/waves. The array can be used, in a multitude of applications including but not limited to: scanning and non-scanning imaging, to excite and collect fluorescence light (linear and non-linear), to perform harmonic generation, to excite and collect reflectance signals, to focus light on a sample to perform for example laser cutting, laser ablation, lithography or photodynamic therapy.

The reflective optical objective according to the present invention advantageously provides a support means for its optical reflectors that minimises loss of the optical signal transferred through the objective.

The reflective optical objective according to the present invention, in the parallel microscopy technique, advantageously permits:

keeping high resolution while increasing the field of view;
improving the ratio of device dimension to field of view, close to one;
confocal imaging; and
an increase of imaging depth in tissue.

The present invention beneficially allows imaging large tissue areas with high resolution, while taking up less space, for example, in the tip of the endoscope. This significantly increases the medical utility of endomicroscopy for performing live-histology (optical biopsy) of living tissue.

The reflective optical objective according to the present invention can have low chromatic and spherical aberration. This is advantageous for non-linear microscopy that works in a wide spectral range and requires a tight focus for efficient fluorescence excitation. Multiplexing the scanning by an array of reflective (micro) objectives of the present invention allows scanning larger sample areas.

Moreover, the reflective optical objective according to the present invention provides high NA (numerical aperture) focusing of light while using a simple optical design and therefore it can advantageously be miniaturized while maintaining good focusing quality. Moreover, light focussing being based on reflection and not refraction makes the reflective optical objective free of chromatic aberration.

The reflective optical objective can be configured/designed in the way to eliminate spherical aberrations and can advantageously be arranged in a two-dimensional array in order to perform large surface parallel scanning.

BRIEF DESCRIPTION OF THE FIGURES

The above object, features and other advantages of the present invention will be best understood from the following detailed description in conjunction with the accompanying drawings, in which.

DETAILED DESCRIPTION

Figure 1A:
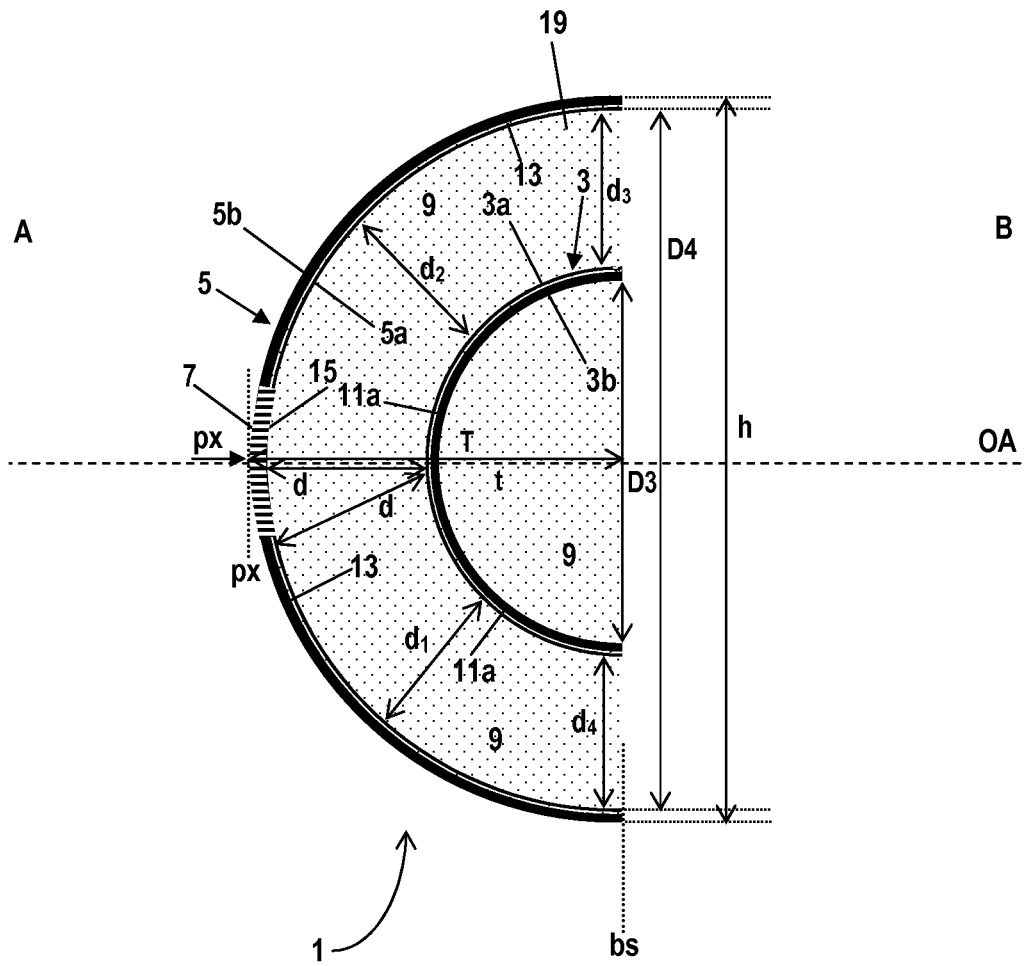
FIGS. 1a, 1b, 1c, 1d and 1e are cross sectional views of examples of a reflective optical objective according to the present invention.
Figure 1B:
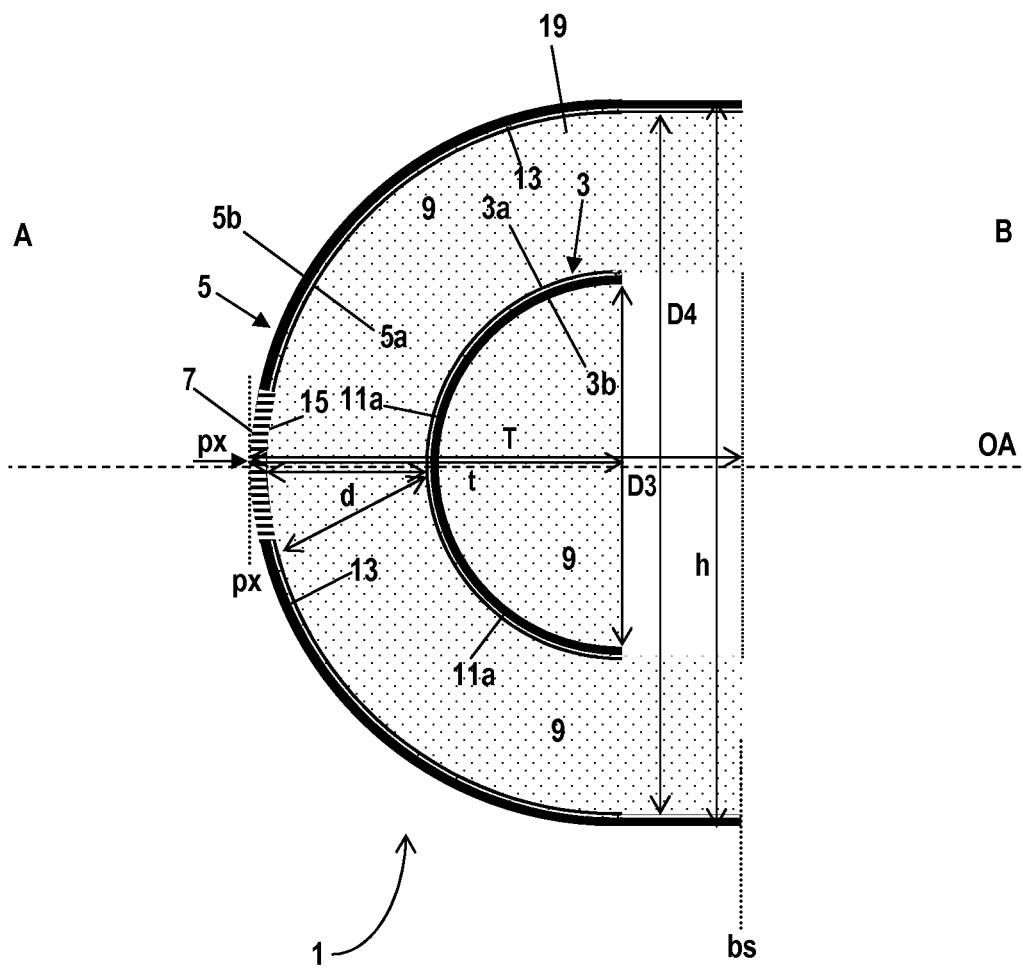
Figure 1C:
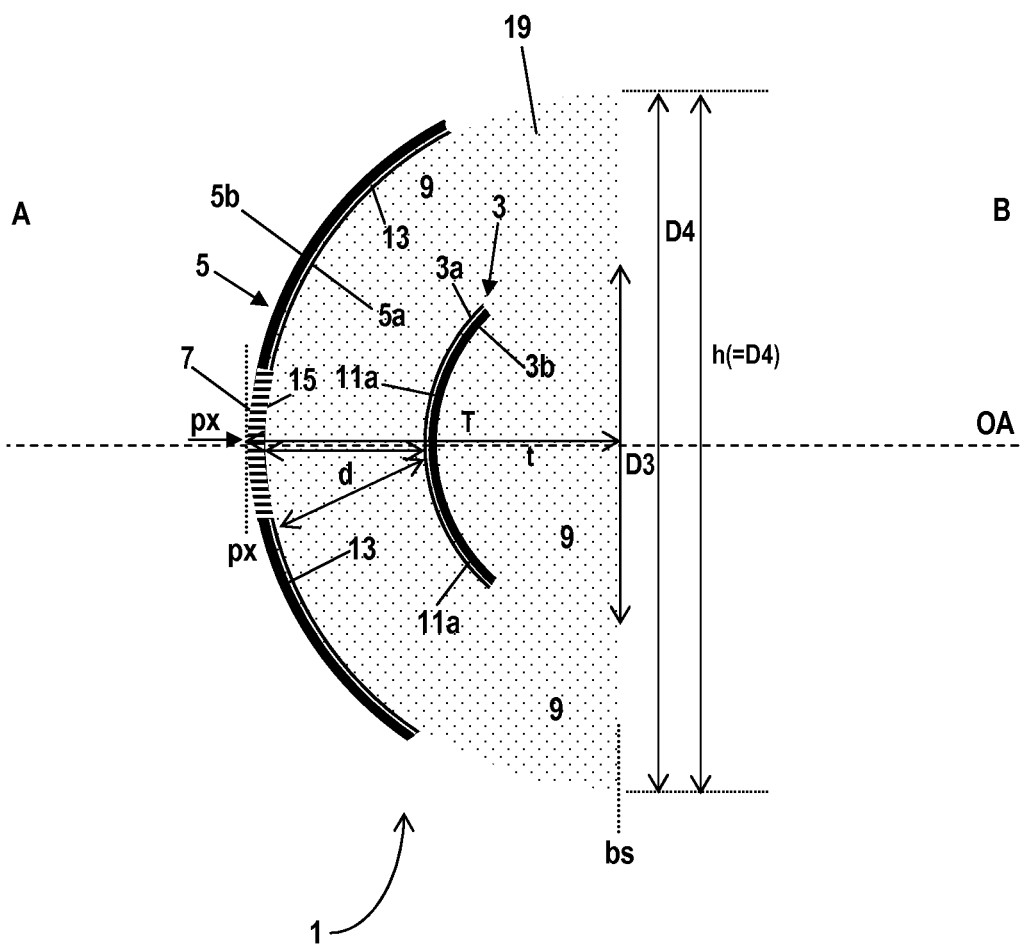
Figure 1D:
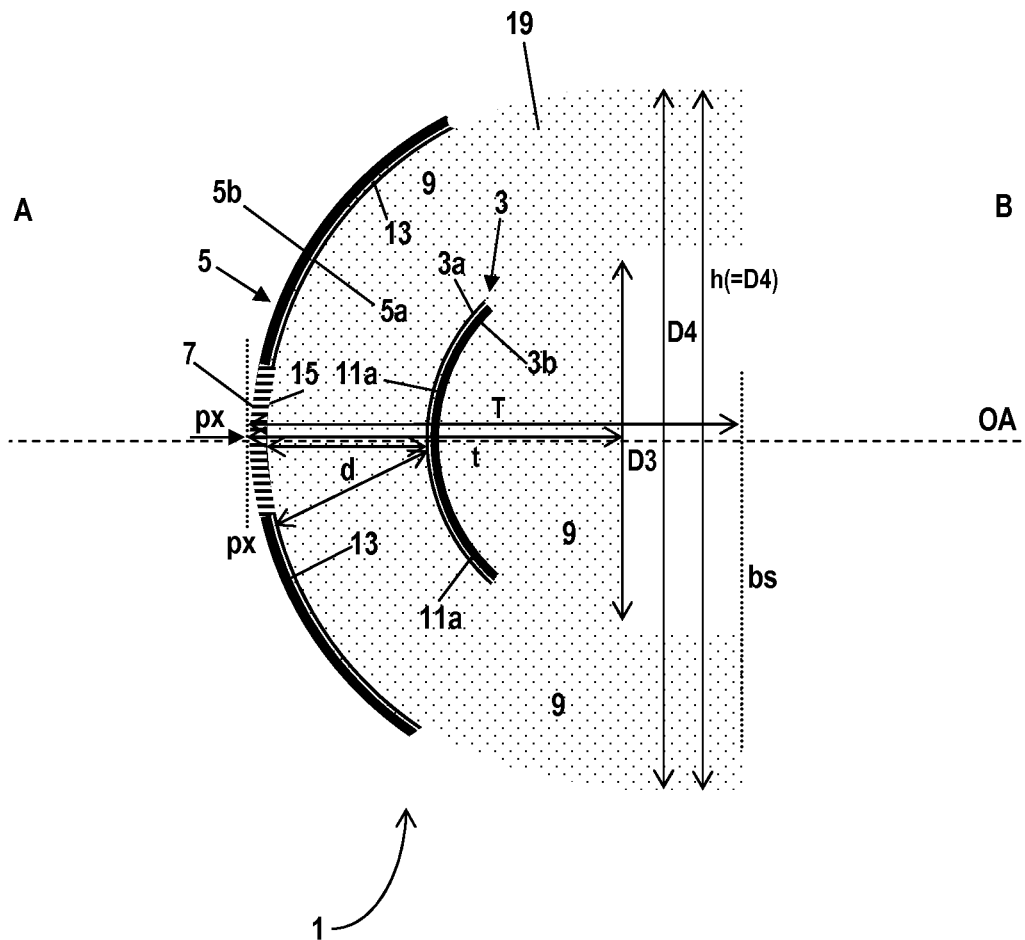

FIGS. 1a, 1b, 1c, 1d and 1e illustrate an example of a reflective optical objective 1 according to the present invention.

The reflective optical objective 1, according to a preferred embodiment of the present invention, includes a first reflecting element 3, a second reflecting element 5, a transmissive section 7 and support or holding means 9.

Figure 1E:
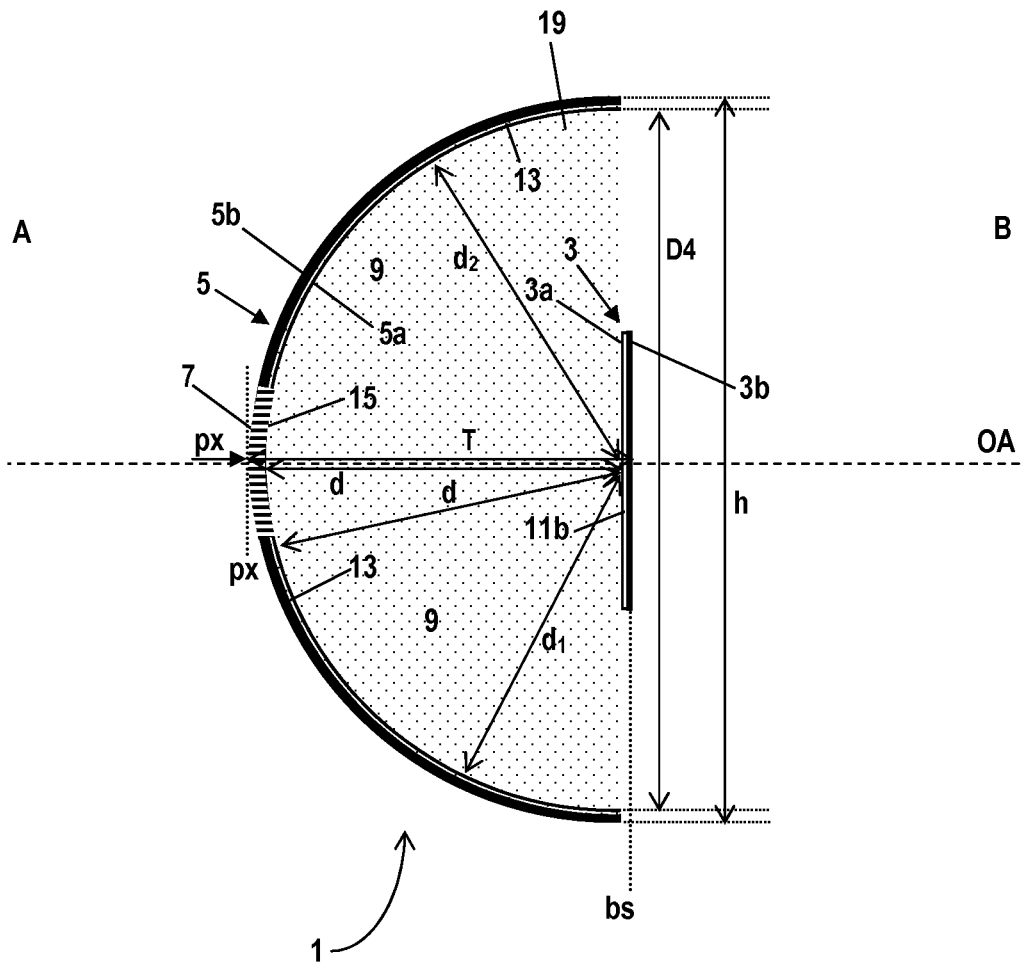

The first reflecting element 3 includes a front surface (or front side) 3a and a back surface (or back side) 3b, and the front surface 3a includes a convex reflecting surface 11a (meaning that the reflective surface is curved and bulges outward towards incident light, for example, incident from side A) or a flat (or planar) reflecting surface 11b (FIG. 1e).

The first reflecting element 3 is also convexly curved in the case where the front surface 3a includes convex reflecting surface 11a (FIGS. 1a to 1d) and is flat (or planar) in the case where the front surface 3a includes a flat reflecting surface 11b. The convex reflecting surface 11a (and the flat reflecting surface 11b) is, for example, formed by a metallic layer/mirror, a dichroic layer or a multilayer stack reflector. In a preferred embodiment of the present invention, the first reflecting element 3 is comprised solely of a metallic layer/mirror, a dichroic layer or a multilayer stack reflector. In the preferred embodiment of the present invention, the first reflecting element 3 is comprised solely of a metallic mirror. Alternatively, the first reflecting element 3 is comprised of a metallic layer/mirror, a dichroic layer or a multilayer stack reflector deposited on an additional layer or structure, or deposited between additional layers or structures.

The second reflecting element 5 includes a front surface (or front face) 5a and a back surface (or back face) 5b, and the front surface 5a includes a concave reflecting surface 13 (meaning that the reflective surface is curved and bulges inward away from incident light, for example, incident from side B).

The second reflecting element 5 is also concavely curved. The concave reflecting surface 13 is, for example, a metallic layer/mirror, a dichroic layer or a multilayer stack reflector. In a preferred embodiment of the present invention, the second reflecting element 5 is comprised solely of a metallic layer/mirror, a dichroic layer or a multilayer stack reflector. In the preferred embodiment of the present invention, the second reflecting element 5 is comprised solely of a metallic mirror. Alternatively, the second reflecting element 5 is comprised of a metallic layer/mirror, a dichroic layer or a multilayer stack reflector deposited on an additional layer or structure, or deposited between additional layers or structures.

The concave reflecting surface 13 of the second reflecting element 5 faces the convex reflecting surface 11a (or the flat reflecting surface 11b) of the first reflecting element 3. The first 3 and second 5 reflecting elements are separated by a fixed distance d. In the embodiment of FIG. 1, the concave reflecting surface 13 of the second reflecting element 5 is separated from the convex reflecting surface 11a (and the flat reflecting surface 11b) of the first reflecting element 3 by the fixed distance d.

Separation distance d between the first 3 and second 5 reflecting elements is the distance d between the first 3 and second 5 reflecting elements measured substantially at the apex (px) (or in the region close the apex) of reflective optical objective 1 (FIG. 1).

Figure 2:
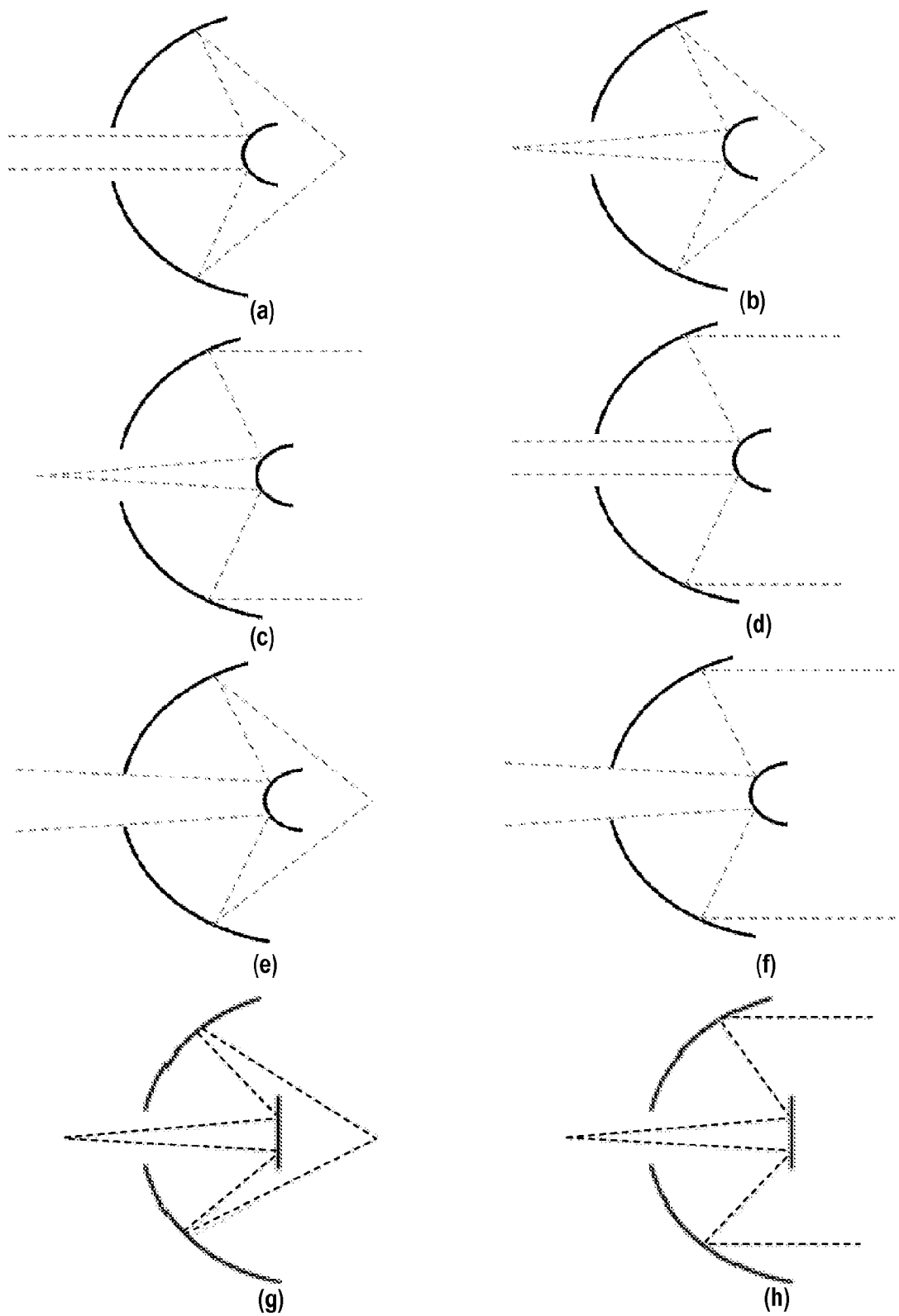
FIG. 2 illustrates examples of different focusing regimes of a reflective optical objective according to the present invention.

Light can, for example, enter the device on one side A and at least part of this light will exit on the other side B (FIGS. 1 and 2). In order for the light incoming on the second reflecting element 5 to reach the first reflecting element 3, the second reflecting element 5 needs to show at least partial transparency for light intensity or a defined light spectrum, on at least a part of its area.

The second reflecting element 5 includes the transmissive section 7 permitting electromagnetic wave/radiation, for example incident from side A (FIG. 1), to pass through and traverse the second reflecting element 5 and the concave reflecting surface 13, and to propagate to the first reflecting element 3, where the electromagnetic wave/radiation is reflected by the convex reflecting surface 11a (or the flat reflecting surface 11b).

The transmissive section 7 can be a layer that at least partially transmits (for example, >50% transmission) the incident electromagnetic wave/radiation from side A. Such a layer can be deposited on a section (for example, whose area is 15% of the area of the back surface 5b, and (symmetric) around common axis OA where the second reflecting element 5 has been removed or is not present (for example, where a mask is used to prevent formation of the second reflecting element 5 at that section). Such a layer could be, for example, an anti-reflection (AR) coating layer.

FIG. 1 illustrates the transmissive section 7 positioned centred about the common axis OA. However, the transmissive section 7 does not necessarily have to be centred and can alternatively be positioned either side of the common axis OA.

Alternatively, the transmissive section 7 can be formed through the removal or absence of a section of the second reflecting element 5 to form an aperture (FIG. 3d), for example, a section (symmetric) around the common axis OA whose area is, for example, 15% of the area of the back surface 5b.

The transmissive section 7 includes a curved concave surface 15 facing the convex reflecting surface 11a (or the flat reflecting surface 11b) of the first reflecting element 3. The curved concave surface 15 has for example the same curvature as that of the second reflecting element 5 and the front surface 5a. In the case where the transmissive section 7 is formed by an aperture, the curved concave surface 15 is formed at the surrounding medium (e.g. air in FIG. 1)/material 9 interface. The transmissive section 7 (curved concave surface 15) is also separated, at the apex (px) of the device 1, from the first reflecting element 3 by the fixed distance d. In the embodiment illustrated in FIG. 1, the transmissive section 7 (curved concave surface 15) is separated, at the apex (px) of the objective 1, from the convex reflecting surface 11a (and the flat reflecting surface 11b) by the fixed distance d.

The present invention thus relates to a micro-optical element 1 that acts as a miniaturised reflective objective, of, for example, the Schwarzschild-type, but not being limited to that, with preferably an overall size between 10 micrometers and 10 millimeters.

That is, the reflective optical objective preferably has a height h (FIG. 1) where 10 µm≤h≤10 mm and a width w (substantially) perpendicular to height h (not-illustrated) where 10 µm≤w≤10 mm.

The height h is measured (for example, cross-sectionally) along the base (bs) or flat side of objective 1 (see FIG. 1, side B). Height h is measured along a line where height h is greatest in value. For example, when the base (bs) has a circular area, height h corresponds to the circular diameter.

Height h may or may not include the thickness of the second reflecting element 5. This depends on whether the reflective optical objective 1 includes a second reflecting element 5 that runs down to the base (bs) of the reflective optical objective 1. This is the case in FIGS. 1a, 1b and 1e and height h (twice) includes the thickness of the second reflecting element 5. This is not the case in FIGS. 1c and 1d and height h does not include the thickness of the second reflecting element 5 but comprises the distance between the outer extremities of the support or holding means 9 (carrier material 9).

Width w is also measured along the base (bs) or flat side of objective 1 and has (substantially) the same value as height h when objective 1 is symmetric in shape, for example, when the first and second reflecting elements 3, 5 are spherical.

However, width w can have a value very much different to that of height h, for example, a cylindrical device (cylindrical lens) can be formed when, for example, w=0.1×h. When objective 1 is non-symmetric, the width w is the shorter of h and w.

The reflective optical objective has a thickness T (FIG. 1) where 5 µm≤T≤5 mm. The thickness T is measured cross-sectionally between the base (bs) or flat side of reflective optical objective 1 and the apex (px) of the reflective optical objective 1 along a line from the apex that is substantially perpendicular to the surface of the base (bs) or flat side of the reflective optical objective 1.

Most preferably, the reflective optical objective has a height h where 50 µm≤h≤1 mm, a width w where 50 µm≤w≤1 mm and a thickness T where 10 µm≤T≤0.5 mm. When the first and second reflecting elements 3, 5 are both curved (FIGS. 1(a) to 1(d), the reflective optical objective most preferably has a height h where 100 µm≤h≤1 mm, a width w where 100 µm≤w≤1 mm and a thickness T where 50 µm≤T≤0.5 mm. When the first reflecting element 3 is flat (FIG. 1(e)), the reflective optical objective most preferably has a height h where 50 µm≤h≤1 mm, a width w where 50 µm≤w≤1 mm and a thickness T where 10 µm≤T≤0.5 mm.

The miniaturised reflective objective, in its simplest form, is composed of two curved, reflective surfaces or layers that are positioned along common axis OA. The common axis OA is, for example, the optical axis of the first reflecting element 3 and/or the second reflecting element 5.

In FIG. 1, the first reflecting element 3 and the second reflecting element 5 are positioned (substantially) symmetrically about the common axis OA. However, it is not necessary that the first and second reflecting elements are positioned symmetrically about the common axis OA for the reflective optical element 1 to function. For example, even when the first and second reflecting elements are shifted from a symmetrical position about the common axis OA towards each other, the reflective optical element 1 still transfers electromagnetic radiation from side A to side B (FIG. 1) and vice versa, albeit in a less efficient manner.

The larger reflective surface or layer (second reflecting element 5) contains transmissive section or aperture 7 or at least one transmissive section or aperture 7. A plurality of transmissive sections or apertures 7 can also be used.

By appropriately choosing a shape for each reflecting element 3, 5 and fixing a distance d between the first and second reflective elements 3, 5, the therefore composed reflective optical objective 1 can be used to collimate and focus light beams and manipulate incident electromagnetic radiation as illustrated in FIGS. 2(a) to (h). The reflective optical objective 1 can, for example, gather electromagnetic radiation on one side and focus the electromagnetic radiation on the other side, or receive collimated (or nearly collimated) electromagnetic radiation on one side, transfer the electromagnetic radiation through the objective, and output collimated electromagnetic radiation at the other side.

The reflective optical objective 1 can focus light in different regimes, for example along the optical axis, depending on the curvatures and respective arrangement and distance of the reflective surfaces. Such regimes could, but not exclusively be: parallel beam to focused spot (FIG. 2(a)), divergent beam to focused spot (or point to point (FIG. 2(b))), divergent beam to parallel beam (FIG. 2(c)), parallel beam to parallel beam (FIG. 2(d)), convergent beam to focused spot (FIG. 2(e)), convergent beam to parallel beam (FIG. 2(f)).

FIGS. 2(g) and 2(h) illustrate a reflective optical objective 1 including a flat reflective element 3 also permitting the light manipulating regimes of FIGS. 2(b) and (c) to be obtained, The first and second reflective elements 3, 5 (and reflecting surfaces 11a, 13) are curved and can be for example conical shaped, spherical shaped, ellipsoidal shaped, paraboloidal shaped, hyperboloidal shaped or other numerically determined curved shape. Both the first and second reflective elements 3, 5 can have the same shape but they can alternatively have different shapes.

A distance d between the first and second reflective elements 3, 5 (and between the transmissive section 7 and the first reflective element 3) is chosen and fixed at a value depending upon the desired operating regime (FIG. 2). That is, an operating regime illustrated in FIG. 2 is determined by setting the distance d to a fixed value so that the first reflecting element 3 is permanently set at a fixed distance from the second reflecting element 5 (and transmissive section 7). For example, the distance d can be set to a value that is 124 μm for the regime (a) of FIG. 2 considering that reflecting surfaces 13 and 11a are spherically curved and concentric with a radius of curvature of respectively 200 μm and 76 μm. In this particular example of concentric spherical surfaces for the first and second reflecting elements, the distance d separating the first and second reflective elements 3, 5 is substantially uniform and the same over the entire reflecting surfaces of the first and second reflective elements 3, 5. That is, distances d, $d_1$, $d_2$, $d_3$, and $d_4$ (see, for example, FIGS. 1a and 1e) are substantially the same.

Preferably, the distance d separating the first and second reflective elements 3, 5 is non-zero.

However, it is not necessary that the separating distance d be substantially uniform and the same over the entire reflecting surface of the first and second reflective elements 3, 5 for the reflective optical objective 1 to function. Even when one portion of the first reflecting element 3 is closer to (or further away from) the second reflecting element 5 than another portion of the first reflecting element, the reflective optical objective 1 still transfers electromagnetic radiation from side A to side B (FIG. 1) and vice versa. Advantageously, by appropriately choosing a shape for each reflecting element 3, 5 and fixing, for example, distances d, $d_1$, $d_2$, $d_3$, and $d_4$ (see FIGS. 1a and 1e) between the first and second reflective elements 3, 5 at different values, the reflective optical objective 1 can operate in a more efficient manner because such a configuration can permit aberrations of the reflective optical objective 1 to be reduced.

The reflective optical objective 1 according to the present invention is a single monolithic element composed of or holding two aligned reflective surfaces or layers. The space in between the two reflective surfaces or layers is filled with a solid or semi-solid (partially solidified) material 9. The solid or semi-solid material 9 is a carrier material that supports or holds the constituent components of the reflective optical objective 1 (first and second reflecting elements 3, 5 and transmissive section 7).

Support or holding means 9 comprises carrier material 9 that is solid or semi-solid (partially solidified) material supporting the first and second reflective elements 3, 5. The solid or semi-solid material 9 permits to hold the first and second reflective elements 3, 5 and serves as a foundation for the first and second reflective elements 3, 5. Support means 9 (solid or semi-solid material 9) allows the first reflective element 3 to be permanently maintained in a position relative to the second reflective element 5 and at a permanent distance from the second reflective element 5.

Figure 3:
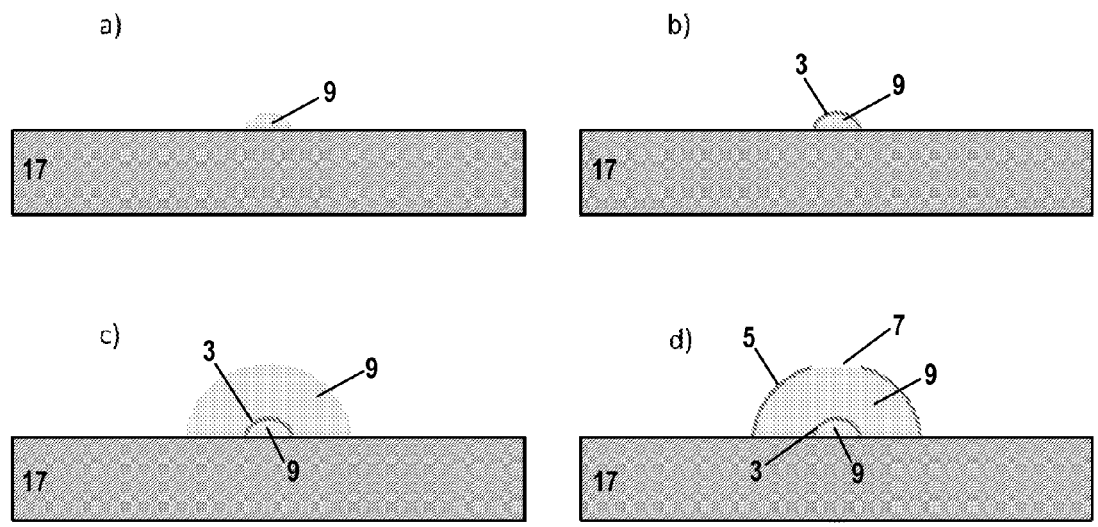
FIG. 3 illustrates different stages of an example of a method for producing a reflective optical objective according to the present invention.

FIG. 3 illustrates an example of a method of fabricating such a monolithic element (reflective optical objective 1) by successively (a) curing a drop of polymer 9 on a substrate 17, (b) covering the drop surface with a reflective coating 3, (c) adding a second drop of polymer 9 (not necessarily the same material) and curing it on top of the previous one and (d) covering the surface of the last drop with a reflective coating 5 including a transparency area 7 (in the center in the embodiment illustrated in FIG. 3). In this example, one of the reflective surfaces or layers (the first reflective element 3) is embedded in the monolithic element 1 as well as the other reflective surface or layer (the second reflective element 5) and optionally this monolithic element 1 (reflective optical objective 1) can then be detached from the substrate 17.

For the reflective optical objective 1 of FIG. 1e, step (a) is not carried out and step (b) consists in depositing the reflective layer 3 on the substrate 17. The second drop of polymer 9 is deposited on the reflective layer 3 and substrate 17, cured and a reflective layer 5 including a transparency area 7 is deposited and formed on the resulting convex surface.

The device is meant to be used with light, i.e. electromagnetic waves/radiation, for example, light in the UV, visible and IR wavelength range. Consequently, the solid or semi-solid embedding material 9 is at least partially transparent for the wavelength or wavelengths of interest.

The position of one reflective surface or layer relative to the other, as well as their respective shape, are fixed and maintained by the solid or semi-solid embedding material 9.

The embedding or carrier material 9 embeds the front surface 3a of the first reflecting element 3 and defines the distance (d, $d_1$, $d_2$, $d_3$, $d_4$) between the first and second reflecting elements 3, 5.

The carrier material 9 thus encloses the front surface 3a and integrates the first reflecting element 3 with the carrier material 9 to unify the front surface 3a with the carrier material 9. The front surface 3a attaches to the carrier material 9. In the examples illustrated in FIGS. 1 and 3, the carrier material 9 embeds (and contacts) the entire area of front surface 3a.

The carrier material 9 also embeds the front surface 5a of the second reflecting element 5 as well as the transmissive section 7. In the example illustrated in FIGS. 1 and 3, the carrier material 9 fully embeds the entire area of front surface 5a as well as the transmissive aperture 7.

In the case where transmissive section 7 is formed by an aperture (FIG. 3), the carrier material 9 extends from the embedded front surface 3a to a location of a virtual front surface of the transmissive aperture 7 corresponding to the position of the front surface 5a of the removed or absent section of the front surface 5a. In other words, extending to a virtual concave surface having the same curvature as that of the front surface 5a and joined to the front surface 5a delimiting the aperture 7.

The carrier material 9 thus fills a cavity 19 delimited by the front surface 5a and the transmissive section 7 (or a virtual front surface corresponding to the position of the front surface 5a of the removed or absent section) on one side, and delimited by the front surface 3a on the other side.

Moreover, in the preferred embodiment of the present invention, the carrier material 9 embeds the convex reflecting surface 11a (or the flat reflecting surface 11b) and the concave reflecting surface 13.

Carrier material 9 also embeds the back surface 3b of the first reflecting element 3 (FIGS. 1a to 1d). Although it is not illustrated in FIG. 1 e, the carrier material 9 can also embed the back surface 3b of the flat first reflecting element 3. In the examples illustrated in FIGS. 1a to 1d and 3, the carrier material 9 embeds (and contacts) the entire area of back surface 3b. The carrier material 9 embedding the back surface 3b can be the same as that embedding the front surface 3a, or can be a different carrier material 9.

Alternatively, the back surface 3b is not embedded by a carrier material 9. No material 9 is present in an inner space delimited by the curved back surface 3b of the first reflecting element 3. Such a reflective optical objective may be produced by employing a patterned substrate 17 including protruding convex curved structures upon which carrier material 9 and then the second reflecting element 5 is deposited. The deposited structure is then removed and the first reflecting element 3 is then deposited in the concave space delimited by the carrier material 9.

Optionally, the back surface 5b of the second reflecting element 5 may also be embedded by carrier material 9.

In the examples illustrated in FIGS. 1 and 3, the carrier material 9 thus completely fills in the space between the first reflecting element 3, and the second reflecting element 5 and the transmissive aperture 7 (delimited by front surface 3a, and front surface 5a and the transmissive aperture 7) and, in FIGS. 1a to 1d, also fills in an inner space delimited by the curved back surface 3b of the first reflecting element 3.

The carrier material 9 is in contact with the front surface 3a of the first reflecting element 3 and the front surface 5a of the second reflecting element 5. The carrier material 9 connects the front surface 3a to the front surface 5a. In the examples illustrated in FIGS. 1 and 3, the carrier material 9 is in contact with the entire area of the front surface 3a and the front surface 5a.

In the examples illustrated in FIGS. 1 and 3, the carrier material is in contact with the convex reflecting surface 11a (or the flat reflecting surface 11b) and the concave reflecting surface 13.

The carrier material 9 is in contact with the entire area of the convex reflecting surface 11a (or the flat reflecting surface 11b) and the concave reflecting surface 13.

The carrier material 9 connects the front surface 3a to the front surface 5a and in the examples illustrated in FIGS. 1 and 3, directly connects the front surface 3a to the front surface 5a. The carrier material 9 directly connects the convex reflecting surface 11a (or the flat reflecting surface 11b) to the concave reflecting surface 13.

Alternatively, the carrier material is in contact with only the convex reflecting surface 11a (or the flat reflecting surface 11b) or the concave reflecting surface 13.

The carrier material 9 is a solid or semi-solid (or partially solidified) material. A semi-solid (or partially solidified) material includes any substance that has a gel-like texture and that is not classified as a fluid or a solid.

The carrier material 9 thus acts to hold the first and second reflecting elements 3, 5 as well as the transmissive section 7 and to maintain and permanently hold the first and second reflecting elements 3, 5 at a distance from each other. The first and second reflecting elements 3, 5 are held and maintained at a distance from each other solely by the carrier material 9.

One example of a method of producing a reflective optical objective 1 and how to fabricate the micro-structures within the miniaturised reflective objective is now described with reference to FIG. 3.

Fabricating a reflective optical objective 1 on a wafer 17 made of silicon, glass, borosilicate, but not limited to these, can be done, although not exclusively, via the following steps:

a) Inkjet-printing of a carrier-material 9, such as a polymer solution, monomer solution, liquid glass, hybrid organic-inorganic materials, sol-gel solutions, photoresist, epoxy materials, or other liquid that can be solidified or semi (partially)-solidified and that is transparent at least in the spectral range of interest. Then, if necessary, curing of the deposited carrier material 9 is carried out. Such inkjet printing can be performed directly onto a non-modified substrate 17, onto a chemically or physically modified substrate (for example using silane chemistry or oxygen plasma treatments), onto a substrate containing a uniform layer including but not limited to polymers, photoresists, metals, silicon derivates (oxides, nitrides, polysilicon, etc.) or onto a substrate containing (micro)structures made of, for example, polymers, photoresists, metals, silicon derivates (oxides, nitrides, polysilicon, etc.). The objective of this step is to form a curved surface on the substrate 17. When seen from the non-substrate side, a structure having an exposed convex surface has been formed by the carrier material 9. Conical, spherical, ellipsoidal, paraboloidal, hyperboloidal or another numerically determined curved shape can be formed by the material 9 (FIG. 3a). The size (on the substrate 17) and shape of the structure formed by the deposited material 9 is determined by the area of the modified (chemically or physically) substrate 17 or the area of the non-modified substrate (e.g. of a platform of the substrate) upon which the carrier material 9 is deposited as well as the surface tension occurring at the surface of the deposited carrier material 9. The thickness of the structure in a direction perpendicular to the surface of substrate 17 can be controlled by controlling the quantity of the deposited carrier material 9.

b) Vapour deposition, e.g. through a prefabricated stencil or in a lift-off process, of a metallic, dichroic, multilayer stack or other reflective layer onto the curved surface of the resulting (micro)structure described under step a). The exposed curved surface of the carrier material 9 can be covered partly or entirely (FIG. 3b). This forms the first reflecting element 3 on the exposed convex surface of the deposited carrier material 9 and the convex reflecting surface 11a.

c) Inkjet-printing of a carrier-material 9, such as a polymer solution, monomer solution, liquid glass hybrid organic-inorganic materials, sol-gel solutions, photoresist, epoxy materials, or other liquid that can be solidified or semi (or partially) solidified and is transmitting light at least in the spectral range of interest, of a (micro)structure that covers the ensemble formed under steps a) and b). Then, if necessary, curing of the deposited carrier material 9 is carried out. Prior to depositing and manufacturing the (micro)structure that covers the ensemble formed under a) and b), the ensemble formed under a) and b) and/or the substrate 17 may be or may be not subject to chemical and/or physical treatments such as silanes chemistry or oxygen plasma. Carrier material 9 is thus deposited onto the first reflecting element 3. This new (micro)structure, covering the ensemble described under a) and b) also forms a curved surface. When seen from the non-substrate side, a structure having an exposed convex surface has been formed by the carrier material 9. Conical, spherical, ellipsoidal, paraboloidal, hyperboloidal or other numerically determined curved shape can be formed by the material 9 (FIG. 3c). The size and shape of the resulting structure is determined by (i) the area of the modified (chemically or physically) substrate 17 or the area of the non-modified substrate (e.g. of a platform at a lower level to the previously mentioned platform) upon which the carrier material 9 is deposited and (ii) the surface tension occurring at the surface of the deposited carrier material 9. The thickness of the resulting structure in a direction perpendicular to the surface of substrate 17 can be controlled by controlling the quantity of the deposited carrier material 9.

d) Vapour deposition, e.g. through a prefabricated stencil or in a lift-off process, of a metallic, dichroic, multilayer stack or other reflective layer onto the curved surface of the (micro)structure described under step c). The exposed curved surface of the carrier material 9 can be covered partly or entirely (FIG. 3d). This forms the second reflecting element 5 on the exposed convex surface of the deposited carrier material 9 and the concave reflecting surface 13, and also forms the transmissive section 7.

The resulting reflective optical objectives 1 can then optionally be removed from wafer/substrate 17 to provide the exemplary reflective optical objectives 1 illustrated in FIG. 1. The reflective optical objective 1 can also remain attached to the wafer/substrate 17 and be individually (or collectively) diced or cut out from the wafer/substrate 17. In such a case, the wafer/substrate 17 should be capable of transmitting light in the wavelength range of operation of the reflective optical objectives 1. Optionally, the wafer/substrate 17 can be thinned down in such a case.

Furthermore, fabrication steps a) and d) could be preceded by other steps, such as deposition of additional functional layers on the wafer 17, functional pre-structuring of parts of the entire layer, depositing of other microstructures such as pillars, platforms, holes, cylinders or curved structures, in order to modify the dimensions of the (micro)structures formed under step a) and step c) or the extent and shape of deposited layers formed under step b) and step d).

As previously mentioned, for the reflective optical objective 1 of FIG. 1 e, step a) is not carried out and in step b) the reflective layer 3 is deposited on the substrate 17. Inkjet printing of carrier material 9 of step c) is then carried out depositing carrier material 9 on the flat reflective layer 3 and substrate 17. Step d) is then carried out and a reflective layer 5 including a transparency area 7 is deposited and formed on the resulting convex surface.

A detailed example of a preferred method of producing the reflective optical objective 1 is now described with reference to FIG. 4.

In a first processing step (FIG. 4(a)), a first platform (Pf1) for the second reflecting element 5 is formed (standard clean room conditions). Spincoating of photo-epoxy GM1060 SU-8 (available from, for example, Gersteltec, Switzerland) on a wafer is carried out to obtain a layer of 5 µm thickness. After spincoating, a pre-bake at 130° C. is carried out and then an exposure to UV with a dose of 70 mJ to form a first platform (Pf1) of substantially circular diameter D4 of 1000 µm using an appropriate mask. A post-exposure bake (PEB) at 95° C. is then carried out.

It should be noted that prior to this step, a surface treatment step using an $O_2$ plasma is performed at 500 W during 7 minutes in order to increase the adhesion of photo-epoxy GM1060 SU-8 during spincoating. Alternatively, a dehydration of the substrate can be done.

In a second processing step (FIG. 4(a)), a second platform (Pf2) for the first reflecting element 3 is formed (standard clean room conditions). Spincoating of photo-epoxy GM1060 SU-8 on the first platform (Pf1) is carried out to obtain a layer of 5 µm thickness. After spincoating, a pre-bake at 130° C. is carried out and then an exposure to UV with a dose of 70 mJ to form the second platform (Pf2) of substantially circular diameter D3 of 100 µm using an appropriate mask. A post-exposure bake (PEB) at 95° C. is then carried out.

A development step is then carried out after 24 hours relaxation time, where propylene glycol methyl ether acetate (PGMEA) is used as a developer and rinsing is carried out using isopropanol (IPA).

A surface treatment step using a silanization process is performed exposing the structure to a triclorosilane in vacuum conditions for 1 hour after an $O_2$ plasma at 30 W during 1 minute.

A first ink-jet printing step (FIG. 4(b)) to form a carrier material 9 structure for receiving the first reflecting element 3 (convex reflecting surface 11a) is then carried out. An inkjet nozzle with a 50 µm diameter aperture is used (commercially available Microdrop ink-jet printing head MD-K-130 and controlling system) to deposit a photosensitive polymeric solution (negative photoresist) based on epoxy (carrier material 9) and to deposit 10 drops of this on the 100 µm diameter first platform (Pf1) that gives an edge angle of 47° (FIG. 4(c)). A pre-bake is then carried out at 100° C. during 30 minutes followed by UV flood exposure during 5 minutes and then a post exposure bake at 160° C. for 30 minutes.

The photosensitive polymeric solution (negative photoresist) based on epoxy is commercially available and developed, for example, by MRT (www.microresist.de) under the name ink-epo. It is a commercially available product having the particularity of being inkjet printable (dedicated for inkjet printing). Such material is inkjet printable at room temperature at viscosity and surface tension values of: Viscosity: 5 to 15 mPa/s and Surface Tension: >35 mN/m.

Figure 4:
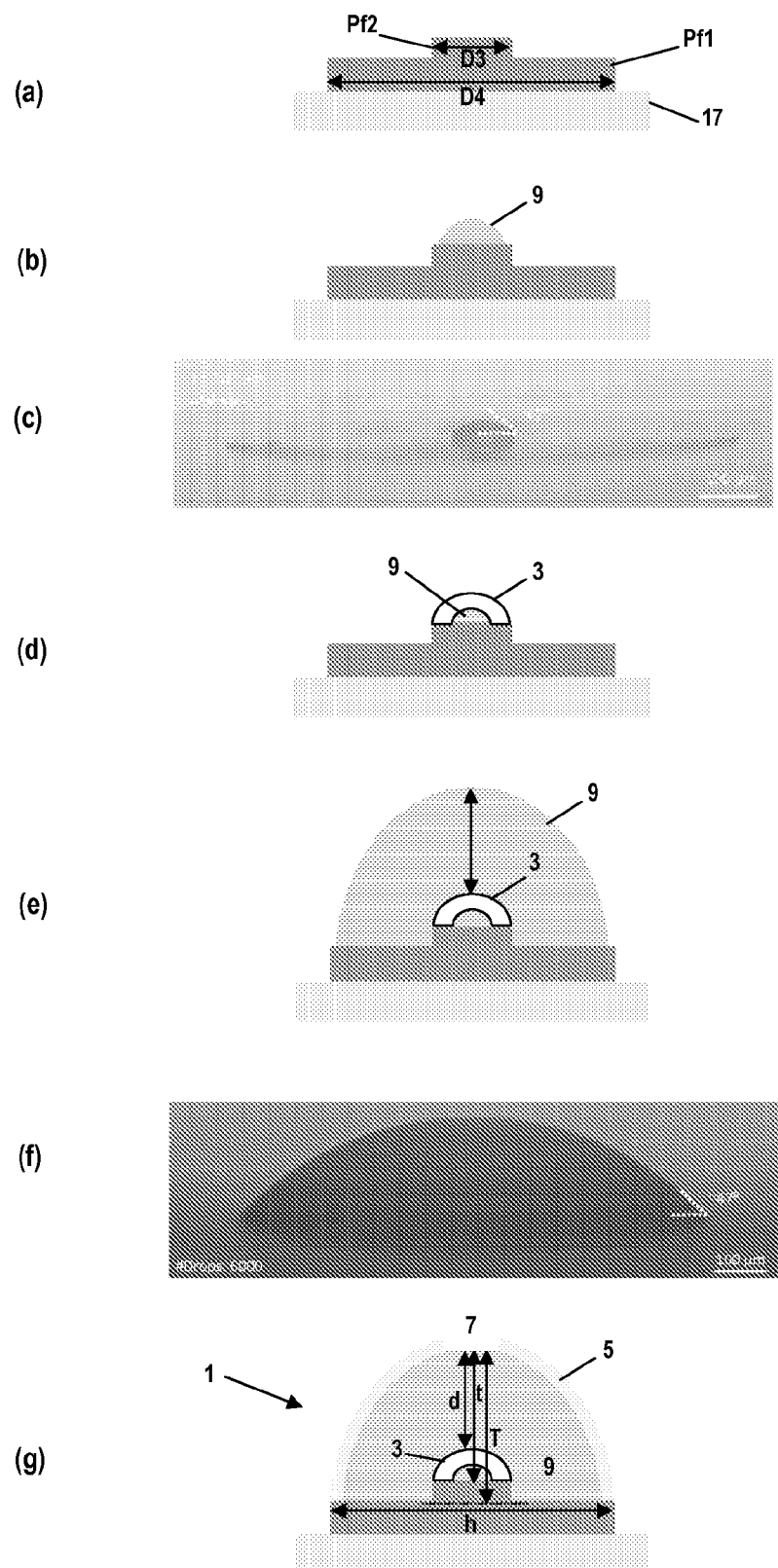
FIG. 4 illustrates a preferred method of producing the reflective optical objective 1 according to the present invention.

A first stencil evaporation step (FIG. 4(d)) to form the first reflecting element 3 (convex reflecting surface 11a) is then carried out. A micro-stencil mask is aligned so as to permit the deposition of aluminium metal of a thickness of 100 nm (via evaporation or sputtering) onto only the exposed convex surface of the previously deposited carrier material 9. It is to be noted that the elements illustrated in FIG. 4 are not to scale and that the thickness of reflecting elements 3 and 5 are exaggerated for ease of understanding.

A second ink-jet printing step (FIG. 4(e)) to form a carrier material 9 structure for receiving the second reflecting element 5 (concave reflecting surface 13) is then carried out. An inkjet nozzle with a 50 µm diameter aperture is used (commercially available Microdrop ink-jet printing head MD-K-130 and controlling system) to deposit the photosensitive polymeric solution (negative photoresist) based on epoxy (carrier material 9) and to deposit 6000 drops of this on the 1000 µm diameter second platform (Pf2) that gives an edge angle of 47° (FIG. 4(f)). A pre-bake is then carried out at 100° C. during 30 minutes followed by UV flood exposure during 5 minutes and then a post exposure bake at 160° C. for 30 minutes.

A second stencil evaporation step (FIG. 4(d)) to form the second reflecting element 5 (concave reflecting surface 13) is then carried out. A micro-stencil mask is aligned so as to permit the deposition of aluminium metal of a thickness of 100 nm (via evaporation or sputtering) onto only the exposed convex surface of the previously deposited carrier material 9 of FIG. 4(e).

The resulting reflective optical objective 1 can then be optionally removed from the support 17, typically using standard technique such as etching of the substrate 17, etching of a sacrificial layer between 17 and platform Pf1 or using thermal chock to separate 17 from Pf1. Moreover, the reflective optical objective 1 can also be optionally removed from the first and second platforms (Pf1, Pf2) using, for example, a sacrificial layer between the two surfaces being separated (that is between the carrier material 9 and platform Pf1 as well as between the carrier material 9 and platform Pf2, (or only a sacrificial layer on the surface of platform Pf1 if detachment from only platform Pf1 is desired).

As indicated above, first (Pf1) and second platform (Pf2) were formed to determine a depositing area for carrier material 9. Alternatively, such platforms are not formed and instead surface treatment (physical or chemical) is used to define a first area for receiving carrier material 9 to form a carrier material 9 structure for receiving the first reflecting element 3 (convex reflecting surface 11a), and to define a second area around the first area for receiving carrier material 9 to form a carrier material 9 structure for receiving the second reflecting element 5 (concave reflecting surface 13).

As previously mentioned, for the reflective optical objective 1 of FIG. 1 e, the first ink-jet printing step (FIG. 4(b)) is not carried out and the first stencil evaporation step (FIG. 4(d)) forms the first reflecting element 3 (flat reflecting surface 11b) on the second platform Pf2 (in fact, only one platform can formed in the processing steps (FIG. 4(a)), the positioning of the deposition of the first reflecting element 3 being determined using a mask), The second ink-jet printing step (FIG. 4(e)) to form a carrier material 9 structure for receiving the second reflecting element 5 (concave reflecting surface 13) is then carried out on the flat reflecting surface 11b and first platform Pf1, and followed by the second stencil evaporation step (FIG. 4(d)) to form the second reflecting element 5 (concave reflecting surface 13).

The height h (FIG. 4(g)) of the reflective optical objective 1 of FIG. 4 is thus approximately 1000 µm and principally determined by the size D4 of the first platform (Pf1), the thickness of the metallic mirror being very small (0.1 µm) in comparison. The separation distance d measured at the apex and between the first and second reflecting elements 3, 5 (and the aperture 7 and first reflecting element 3) is 190 m. The separation distance d principally depends on the number of drops of the carrier material 9 that is deposited and on the surface tension of the carrier material being used. The distance t which is the distance measured at the apex and between the second reflecting element 5 (or the aperture 7) and the base of the carrier material upon which the first reflecting element 3 is deposited is 122 µm. Finally the thickness T (as defined above with respect to FIG. 1) of the reflective optical element 1 of FIG. 4 is 127 µm. The thickness T thus principally depends on the number of drops of the carrier material 9 that is deposited and on the surface tension of the carrier material being used. The shape of the first and second reflecting elements 3, 5 can be controlled using the number of drops of the carrier material 9 that is deposited, by modifying the surface tension or by using a different carrier material 9.

The below Table 1 provides the values for the above mentioned parameters for different reflective optical objectives 1. The below Table 2 provides the values for the above mentioned parameters for different reflective optical objectives 1 including a flat first reflecting element 3 (the number of drops deposited on the second platform Pf2 is thus zero in the first ink-jet printing step and drops are only deposited in the second ink-jet printing step on both platforms). The height h and the thickness T of a reflective optical objective 1 can be measured, for example, using an optical microscope.

TABLE 1

| Pf1 Diameter D4 (µm) | Drop (#) | Pf2 Diameter D3 (µm) | Drop (#) | d(µm) | t(µm) | T(µm) |
|---|---|---|---|---|---|---|
| 1000 | 6000 | 100 | 10 | 190 | 212 | 217 |
| 1000 | 10000 | 100 | 5 | 310 | 320 | 325 |
| 1000 | 20000 | 100 | 5 | 485 | 495 | 500 |
| 450 | 1400 | 50 | 4 | 100 | 125 | 130 |
| 100 | 10 | 50 | 4 | 20 | 45 | 50 |

TABLE 2

(flat mirror case)

| Pf1 Diameter D4 (µm) | Drop (#) | Pf2 Diameter D3 (µm) | Drop (#) | d(µm) | t(µm) | T(µm) |
|---|---|---|---|---|---|---|
| 1000 | 6000 | 100 | 0 | 212 | 212 | 217 |
| 1000 | 10000 | 100 | 0 | 320 | 320 | 325 |
| 1000 | 20000 | 100 | 0 | 495 | 495 | 500 |
| 450 | 1400 | 50 | 0 | 125 | 125 | 130 |
| 100 | 10 | 50 | 0 | 45 | 45 | 50 |
| 50 | 1 | 20 | 0 | 5 | 5 | 10 |

In the ink-jet printing step to form carrier material 9 structures for receiving the first or second reflecting elements, an inkjet nozzle of 50 µm diameter aperture is used. However, inkjet nozzles of smaller diameter are available and when used as set out above permit to produce reflective optical objectives 1 having a height h down to 10 µm or further and a thickness T down to 5 µm or further.

Figure 5:
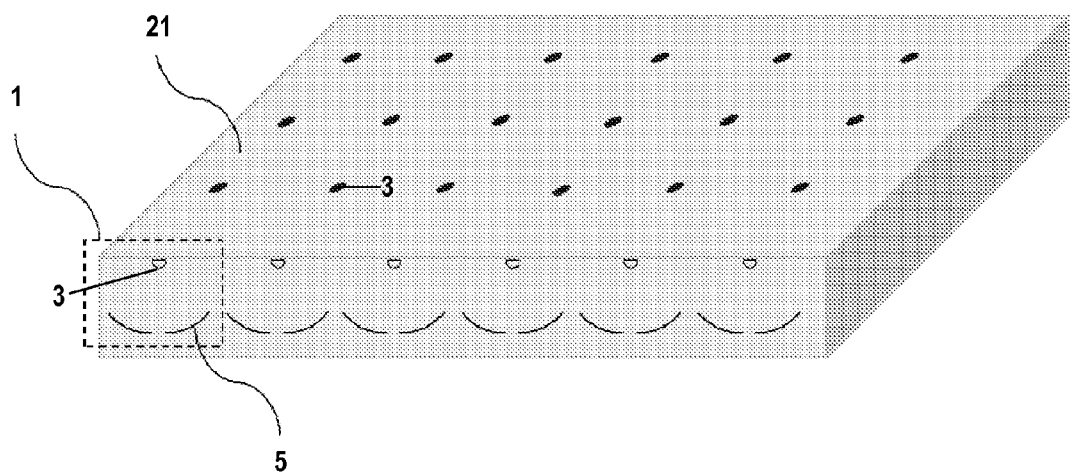
FIG. 5 illustrates an example of a planar array for imaging including the reflective optical objectives according to the present invention.

The reflective optical objectives 1 may be implemented into a two-dimensional, planar, cylindrical, spherical or otherwise curved array 21 (FIG. 5). The arrangement in such an array 21 may be, but is not limited to, rectangular or hexagonal pattern. Optionally, such an array of reflective optical objectives 1 is immersed in a polymer solution, monomer solution, liquid glass or other liquid that can be solidified or semi-(partially) solidified and is transparent at least in the spectral range of interest. Once solidified, the array 21 of reflective optical objectives 1 fixed in this supportive layer can be detached from the fabrication wafer. Conversely, the reflective optical objectives 1 can be fabricated directly into a flexible substrate or a rigid substrate containing a flexible layer from which it can be detached. Then, for both configurations, the reflective optical objectives 1 can be implemented into devices of interest. A two-dimensional array 21 of miniaturised reflective micro-objectives may thus be embedded in a flexible or rigid, and planar or bent layer.

Manufacturing of the array 21 can be performed using and or combining one or several techniques of printing, lithography, chemical and physical deposition, ablation, laser polymerisation, direct write laser, and replication, which includes but it is not limited to: inkjet printing, photolithography, stencil lithography, thin metal deposition, chemical vapour deposition, laser ablation, diamond ablation, soft-lithography and nano-imprint lithography.

The array 21 can be used in a multitude of applications including but not limited to: scanning and non-scanning imaging, to excite and collect fluorescence light (linear and non-linear), to perform harmonic generation, to excite and collect reflectance signals, to focus light on a sample to perform for example laser cutting, laser ablation, lithography or photodynamic therapy. The reflective optical objectives 1 can be designed with particularly low chromatic and spherical aberration, providing an advantage for non-linear scanning microscopy that works in a wide spectral range and requires a tight focus for efficient fluorescence excitation.

A concrete example of imaging favours the use of all the reflective optical objectives 1 within an array 21 to create individual focal spots and image simultaneously a large-surface by means of parallel scanning. Arrays 21 can be scaled to the size of the field of view of the image to be achieved. The imaging resolution is determined by the scanning step and the optical resolution of the reflective optical objective 1. Using scanning laser microscopy approaches or other microscopy methods, arrays 21 can image areas of the size of the array 21, without increasing the overall scanning time.

Additionally, the array 21 can be embodied in a (bench-top) microscope, allowing to image areas of several square-centimeters. The array 21 can also be embodied in compact imaging scanners, or in miniaturised, handheld microscopy probes, which are compatible with standard medical endoscopes—both, flexible and rigid.

The reflective optical objective 1 can be combined with a micro-lens, for example, to even further improve focusing performance. Similarly, the array 21 of reflective optical objectives 1 can be combined with a plurality of micro-lens. A description of applications employing the present invention is now presented.

Microscopy Imaging System:

In a (bench-top) microscope the array 21 replaces the conventional microscope objective. With appropriate multiplexing and coupling optics the array 21 can be used for a variety of microscopy methods, such as but not limited to: Confocal microscopy, non-linear microscopy, phase contrast microscopy, dark field microscopy or luminance field microscopy.

Figure 6:
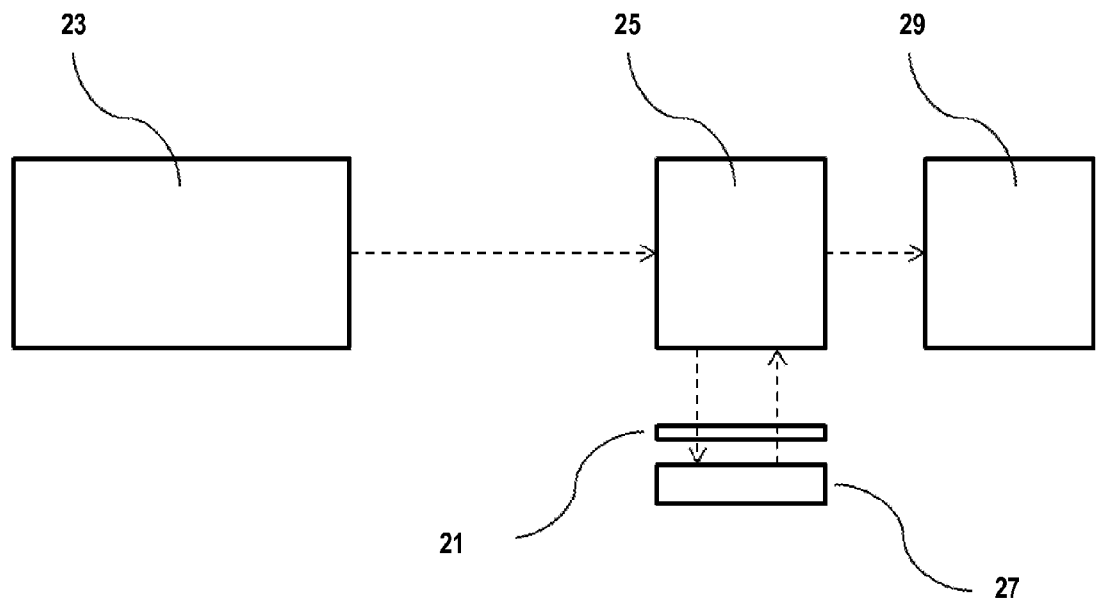
FIG. 6 illustrates an example of a microscope including an array of reflective optical objectives according to the present invention.

FIG. 6 shows a general arrangement for the implementation of an array 21 into a (bench-top) microscope, with the array 21 as a focusing and light collecting element. The light source 23, such as but not limited to a laser, laser diode, pulsed laser, LED or halogen lamp, sends the light beam to coupling optics 25, composed of, but not limited to: collimating systems, dichroic mirrors, filters, mirrors, waveguides and lenses. The light beam is further coupled onto the array 21, which optionally can be combined with a plurality of micro-lenses, and focused at the sample of interest 27. Signal light coming from the sample, such as reflectance, fluorescence, harmonic generation signals or other, is collected by the array 21 (and optionally the plurality of micro-lenses), and sent further to the coupling optics 25. From there it is redirected to a detector array 29, such as but not limited to: CCD or CMOS photodetectors, photodiodes, phototransistors, avalanche photodiodes, photoresistors, Golay cells, bolometer thermopiles, or pyroelectric detectors.

Figure 7:
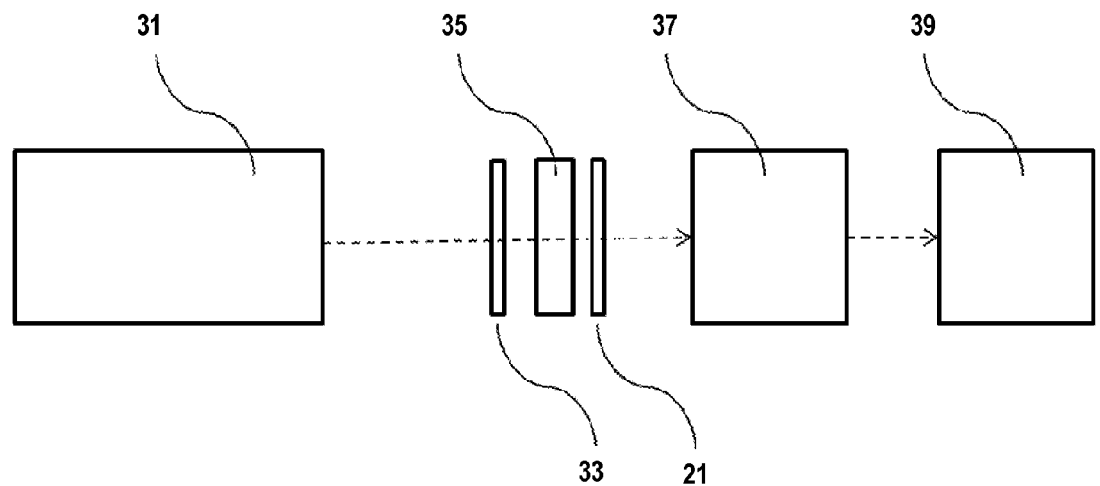
FIG. 7 illustrates an example of a transmission microscope including an array of reflective optical objectives according to the present invention.

FIG. 7 shows a general arrangement for the implementation of an array 21 into a (bench-top) transmission microscopy configuration, where the array 21 acts as the signal collecting element. Here the light source 31, such as but not limited to a laser, laser diode, pulsed laser or halogen lamp, sends the light beam to the collimating or/and focusing system 33. The collimated or focused light beam interacts with the sample 35 and is then collected as signal light by the array 21. Filtering and coupling optics 37 prepare and send the signal collected by the array 21 to the detector array 39. The detector array 39 can be but is not limited to: CCD or CMOS photodetectors, photodiodes, phototransistors, avalanche photodiodes, photoresistors, Golay cells, bolometer thermopiles, or pyroelectric detectors.

Integrated Scanning Head:

The optical relay between reflective optical objectives 1 and sensing elements for detection of the light may have a significant footprint on the overall apparatus size described in the previous microscopy imaging system. Hereinafter, an apparatus is described where the reflective optical objectives 1 are directing the light from the imaging plane towards a sensing element without an intermediary optical system. In this assembly, reflective optical objectives 1 and sensing elements are combined in a fixed configuration that can be moved relatively to a surface, a sample for instance. This configuration results in a more compact apparatus capable of being more easily displaced in front of the object of interest.

Figure 8:
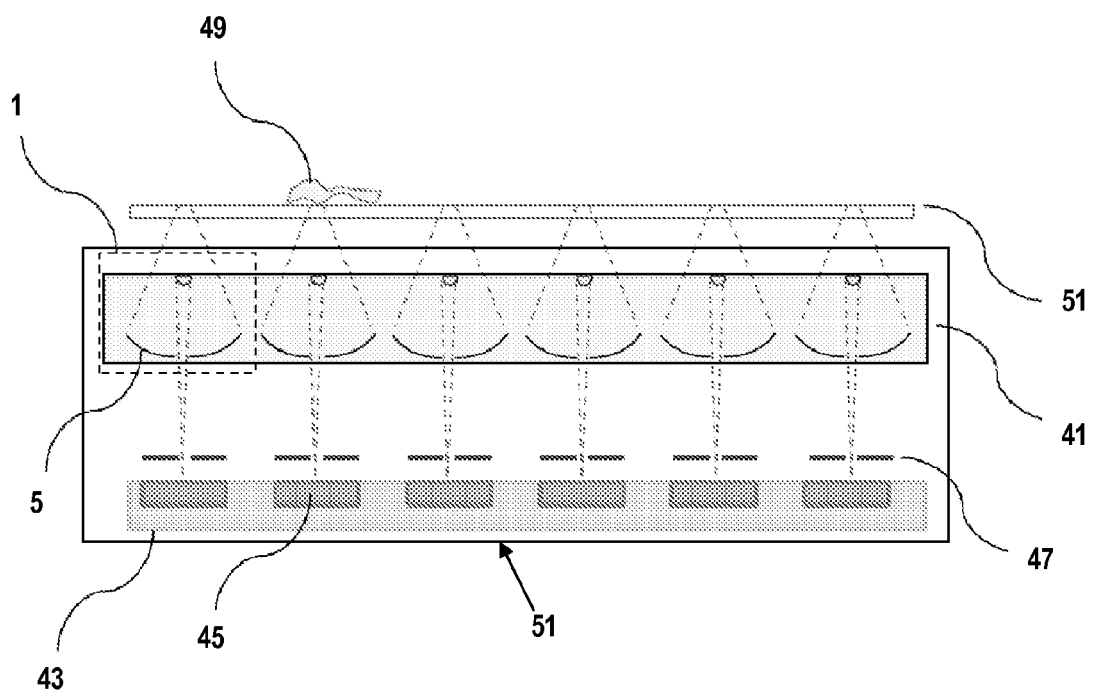
FIG. 8 is a cross sectional view of a scanning head including reflective optical objectives according to the present invention.

FIG. 8 shows the association of a one-dimension reflective optical element array 41 and a linear sensor 43 composed of several sensor elements or sensitive areas 45. Linear sensor 43 can additionally include at least one light emitter, such as for example a LED to illuminate a sample. The respective position of these two parts is fixed and an array of pinholes 47 may be used to select the light of interest. This ensemble corresponds to a device dedicated to collect light coming from the sample 49, e.g. a cell, lying on the surface of the substrate 51, e.g. the bottom of a petri dish, and to detect it with the corresponding sensor. Each reflective optical objective 1 is then associated to a detector area, possibly in a confocal manner due to the array of pinholes 47. Such a device can be used to scan sample 49 and is referred to in the following as a scanning head 51.

Figure 9:
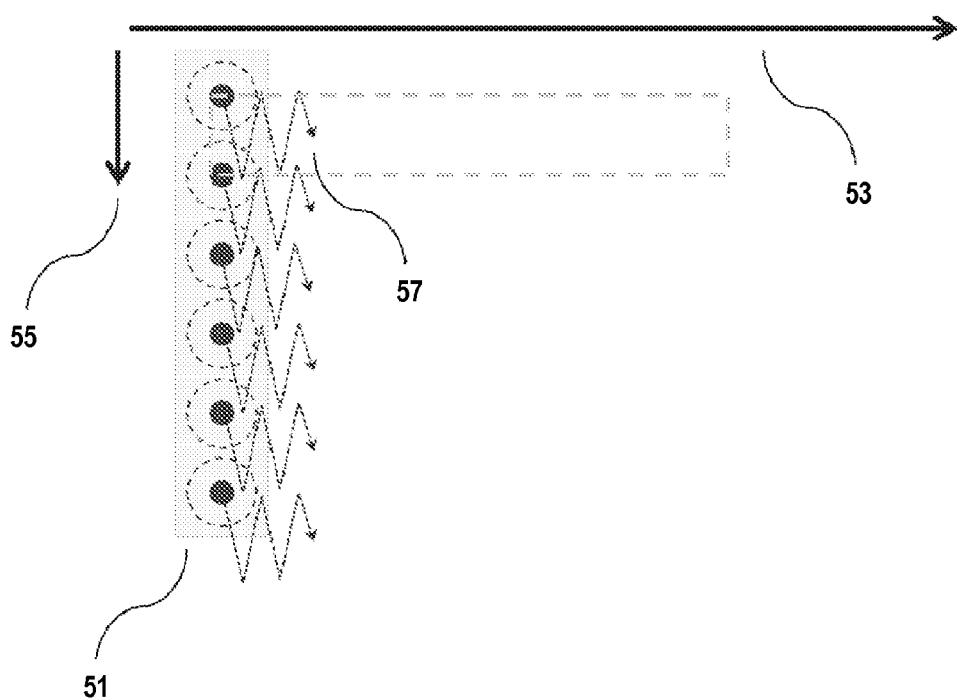
FIG. 9 is a top view of an example of a scanning pattern of the scanning head of FIG. 7.

In FIG. 9, the scanning head 51 is displaced in a plane by means of a two axis scanning stage. The slow axis 53 is moving the scanning head 51 in one direction while the fast axis 55 implies a periodic displacement allowing the scanning head 51 to oscillate along the fast axis 55. As a result, each reflective optical objective 1 composing the array 41 will scan the plane along a band containing a multitude of acquisition points 57. In this way, such a scanning head 51 with the appropriate rate of acquisition provides a set of measurements that allow image reconstruction of a sample within the imaging plain.

A one-dimension array was used to facilitate the clarity to the description; however, the use of a two-dimension array is preferred.

Such an apparatus can be used in applications where the compactness of the all imaging system is a criterion of interest and when it is preferable to move the apparatus rather than the sample under investigation. Scanners for histology or for cell culture monitoring are, for example, applications of interest.

Endomicroscope—Hand-Held, Miniaturised Scanning Microscope Confocal or Multiphoton, for Applications in Endoscopy:

The present invention also relates to the use of the array 21 including a plurality of reflective optical objectives 1 in an endoscope or endomicroscope for imaging, in particular, in-vivo imaging.

A microscope for endoscopy, laparoscopy or open neurosurgery, for instance neurosurgery, termed endomicroscope, has to fulfil conditions in terms of overall device size. The available space in the distal part of an endoscope is limited and a compromise has to be found for the space requirements of functionalities. An endomicroscope is either integrated in the endoscope or is inserted as an add-on device through the working channel of the endoscope. The medical application field (such as neurosurgery, surgery, gastroenterology, pulmonology, urology, gynaecology etc.) of the endoscope determines the size of the distal end of the endoscope and consequently the diameter available for the endomicroscope. A typical endoscope in Gastroenterology has an overall diameter of 1 cm to 1.5 cm at the distal end and a working channel of 2 mm to 4 mm. These are the dimensions to be considered for a probe-based endomicroscope to be inserted through the working channel of an endoscope.

In both cases of probe-based and integrated endomicroscope, only the necessary parts are kept in the distal end of the endomicroscope and all other elements are built in at the proximal end, which remains outside of the patient.

Figure 10:
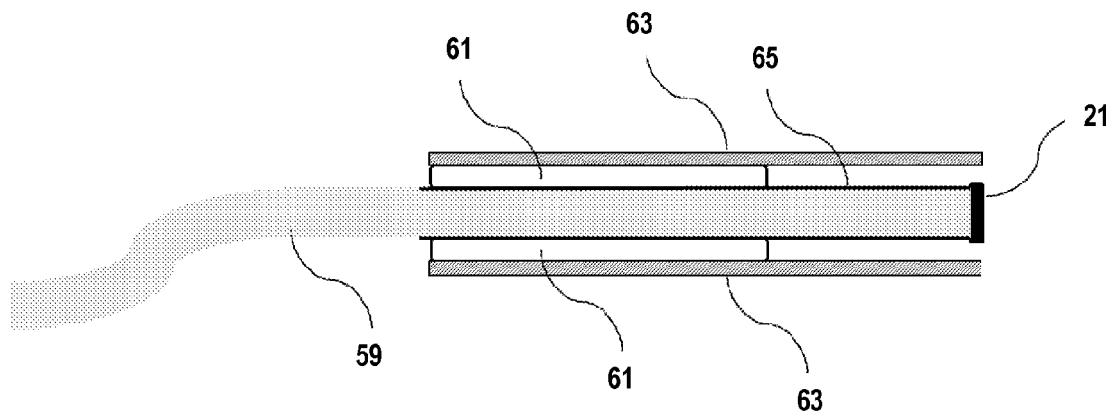
FIG. 10 is a cross sectional view of a distal head of an Endoscope/Endomicroscope including an array of reflective optical objectives according to the present invention destined to be inserted or integrated into the Endoscope/Endomicroscope.

FIG. 10 shows an example integration of the array 21 in the distal end of an endomicroscope. The excitation light is carried by a flexible bundle of light wave-guides 59 and delivered to the array 21 (which optionally can be combined with a plurality of micro-lenses). The flexible bundle of light wave-guides can be, but is not limited to, a bundle of single mode optical fibres, a bundle of multi-mode optical fibres, a bundle of photonic band-gap fibres, a bundle of double-clad fibre, a multi-core imaging fibre or other structured optical wave-guide. As mentioned, collimating micro-optics (micro-lenses) can optionally be included between the flexible bundle of light wave-guides 59 and the array 21. Each wave-guide of the bundle is connected to one reflective optical objective 1 within the array 21. The array 21 focuses the excitation light and when brought in proximity of the tissue of interest, signal light, such as, but not limited to reflectance, fluorescence or harmonic signals, is produced. The signal light is collected through the array 21 and coupled back into the flexible bundle of light wave-guides 59.

A scanning laser endomicroscope needs a micro-actuator to scan the entire image surface. Here a micro-actuator 61, such as a three-axis piezo-scanner, a tubular piezo-scanner with optionally an additional axial actuator, a three-axis galvanic motor, step-micro-motors, a three-axis MEMS scanner or two-axis versions of all of the above, is attached to the outer housing 63 of the distal head of the endomicroscope, and moves the inner housing 65 including the light wave-guide 59 and the array 21 according to a pre-programmed trajectory. The inner housing 65 provides mechanical stability for the fibre bundle and the array 21. Using the array 21, it is sufficient to scan the surface corresponding to one reflective optical objective 1 in order to obtain an image size comparable to the size of the array 21.

Figure 11:
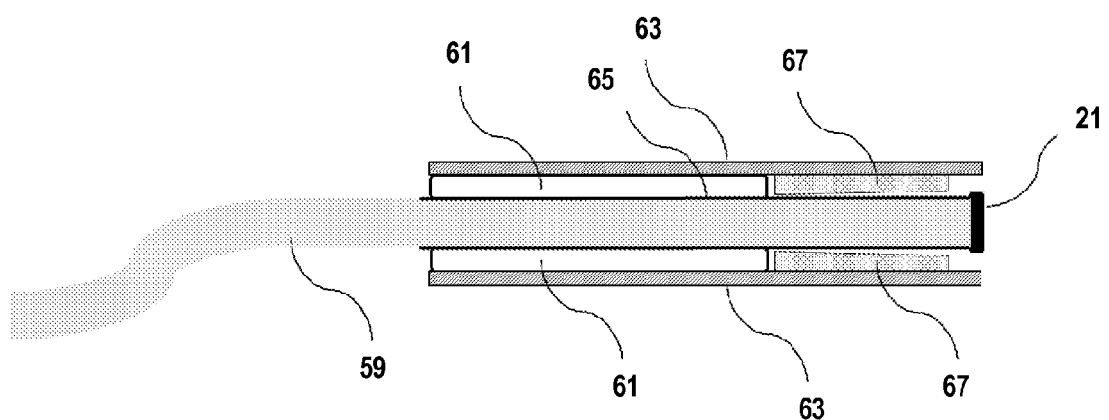
FIG. 11 is a cross sectional view of a distal head of FIG. 9 further including a sealing element.

FIG. 11 shows a version of the distal head with some additional features. In order to protect the internal components of the distal endomicroscope head from fluids, biological material, microorganisms and other external substances in a clinical environment a sealing element 67 is added between the inner housing 65 and the outer housing 63. It can optionally be disposable, if sterilisation is not possible. Furthermore, the distal head can contain a plurality of channels that allow for creating and releasing suction. Such a feature is fixes the distal endomicroscope head temporarily to the tissue of interest. Fixing the distal endomicroscope head temporarily to the tissue of interest contributes to stabilisation during the imaging process and reduces motion artefacts, which are common in living patients, due to heart beat, breathing or spontaneous tissue motion.

Figure 12:
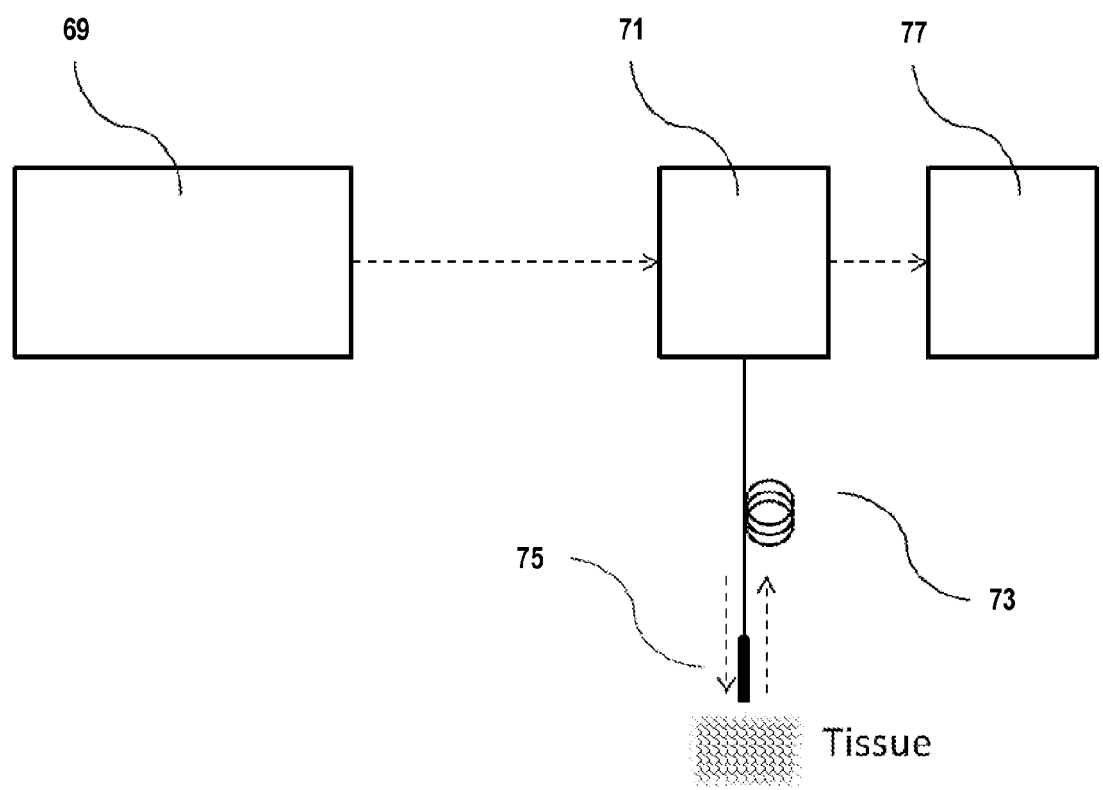
FIG. 12 illustrates an overall system view of an Endoscope including proximal optics and the distal endoscopic head of FIG. 9 or 10.

The overall endomicroscopy system using an array 21 is presented in FIG. 12. The light source 69, such as but not limited to a laser, laser diode, pulsed laser, LED or halogen lamp, sends the light beam to coupling optics 71, composed of but not limited to: collimating systems, dichroic mirrors, filters, mirrors, waveguides, group velocity dispersion compensating system and lenses. The excitation light beam is further coupled into the flexible bundle of light wave-guides 73 that guides that light to the distal endomicroscope head 75 described previously.

Signal light excited or produced in the tissue of interest, such as reflectance, fluorescence, harmonic generation signals or other, is collected by the array 21 in the distal endomicroscope head 75 coupled back into the flexible bundle of light wave-guides 73, where it is guided back to the coupling optics 71. There signal light is separated from excitation light and sent to a detector array 77, such as but not limited to: CCD or CMOS photodetectors, photodiodes, phototransistors, avalanche photodiodes, photoresistors, Golay cells, bolometer thermopiles, or pyroelectric detectors.

For a confocal scanning endomicroscope each light wave-guide core functions as an individual pinhole.

For a multiphoton scanning endomicroscope the light source 69 should be a pulsed laser, ideally a femtosecond NIR laser. A dispersion precompensation element is necessary within the coupling optics 71 to precompensate the group velocity dispersion (GVD) induced by the bundle of light wave-guides 73. This GVD precompensation element could be, but is not limited to, a photonic core fibre with a negative GVD and the appropriate length to compensate the dispersion induced by the bundle of light wave-guides 73.

Using reflective optical objectives 1 in a multiphoton imaging system, the fluorescence or harmonic signal can be collected via the same optical pathway. In the case where dichroic reflective surfaces are used to build the reflective optical objectives 1, the signal spectral band traverses the reflective surfaces and is collected by refraction.

The scanning pattern of the micro-actuator 61 and the image acquisition of the detector array 77 are controlled by a computer (not illustrated). Image analysis algorithms can be used to analyse objectively tissue structure, such as the micro-vascular distribution in the tissue. The goal thereof is to establish objective selection criteria that distinguish healthy from neoplastic/cancerous tissue during on-going clinical procedures, for instance for purposes of disease diagnosis, malignancy staging, or malignancy margin delineation.

Large Surface Microscope for Tissue Examination in Dermatology, Surgery, Key-Hole Surgery or ORL:

A microscope for tissue examination in dermatology surgery, key-hole surgery or ORL does not face constraints in terms of device dimensions, as strict as in endoscopy. However, the increase of the image area provides the benefit of examining large surfaces at shorter duration of the examination.

Figure 13:
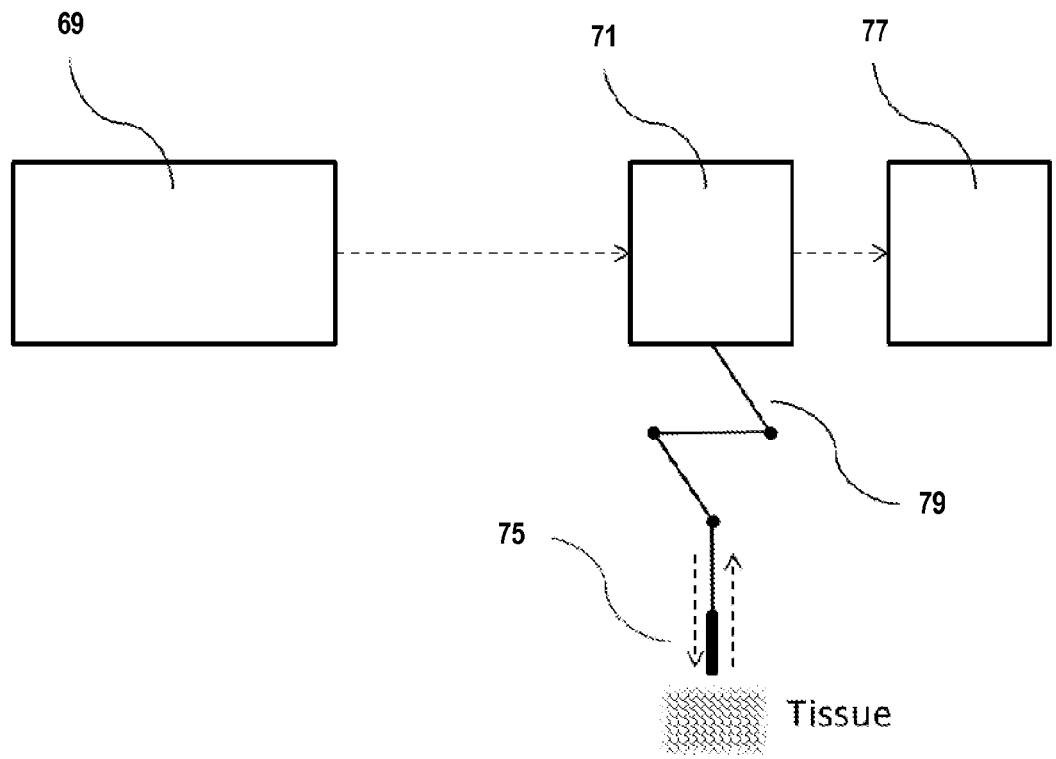
FIG. 13 illustrates a microscope for dermatology including a distal head comprising an array of reflective optical objectives according to the present invention.

FIG. 13 shows an example embodiment of a microscope for tissue examination in dermatology or ORL. The distal head 75 here does not have dimension restrictions and can contain an array 21 of area sizes in the order of square centimeters. The waveguide 79 can be either implemented in a flexible arm or rigid arm with deviation ankles, in order to position the distal head 75 at the skin or mouth mucosa patch of interest. In the case of a rigid arm, the waveguide 79 could be a bundle of single mode optical fibres, a bundle of multi-mode optical fibres, a bundle of photonic band-gap fibres, a bundle of double-clad fibre, a multi-core imaging fibre or other structured optical wave-guide, or a hollow space that transmits the excitation and signal light according to ray optics.

Figure 14:
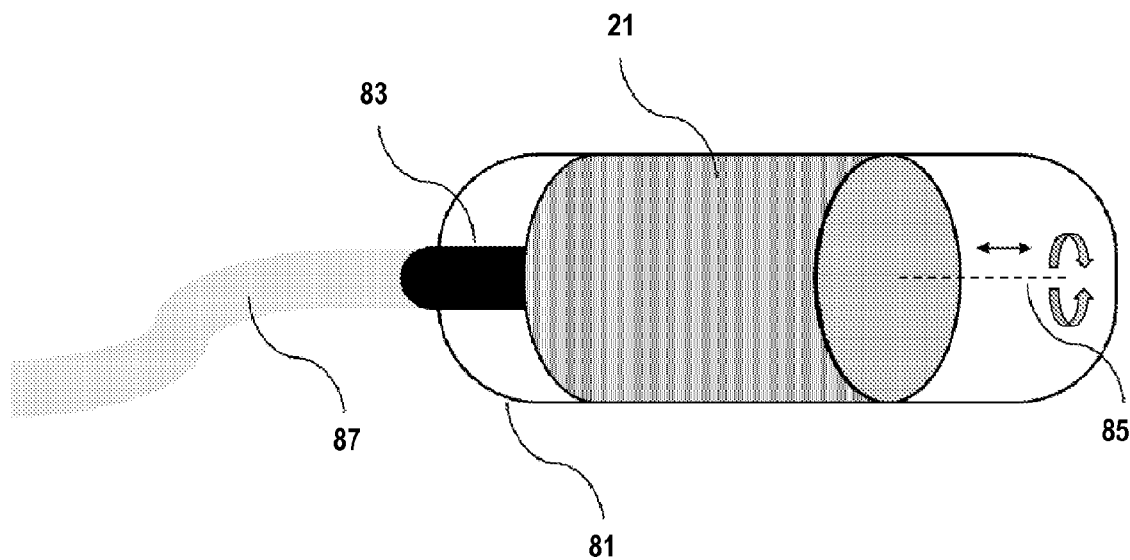
FIG. 14 illustrates a balloon catheter, for example, for large surface live histology.

Balloon-Catheter, Imaging Fluorescence in Living Tissue with Cellular Resolution for Live Histology of Large Tissue Surfaces:

The herein proposed balloon-catheter (FIG. 14) includes preferably:
(i) a flexible balloon 81, which can be blown up in order to flatten the surface of a tubular body cavity, like for instance the esophagus or colon;
(ii) a large bent (flexible)array 21 that can be shaped as a cylinder or a partially closed cylinder, for instance a quarter or a half cylinder;
(iii) a motor 83 that can move array 21 either forth and back along the axis 85 of the array 21 and/or turn it axially in both directions, in order to scan a large surface of the organ of interest; and optionally
(iv) a bundle of fibers 87 for light delivery to and harnessing light from every reflective optical objectives 1 within array 21.

Such a balloon-catheter can image rapidly with cellular resolution large surfaces of tubular body cavities and obtain a histological tomography of the living tissue inside the patient.

The balloon catheter can be used with a similar setup as described in FIG. 12, where the balloon catheter replaces the endomicroscope head 75.

Large Surface Scanner for Digital Pathology:

A large surface scanner for digital pathology includes either the previously described microscope illustrated in FIG. 6 or the previously described microscope illustrated in FIG. 7, combined with an automatic sample loading and imaging system. Such a resulting system automatically images a large set of histological slides, in order to digitalize the histological slices for examination by a pathologist.

Large Surface Scanner for Surface Quality Control within an Automatized Micro-Manufacturing Process:

A large surface scanner for surface quality control within an automatized micro-manufacturing process is composed of the previously described microscope illustrated in FIG. 6 or the previously described microscope illustrated in FIG. 7, combined with an automatic sample loading or transferring system and an automated imaging system. The resulting system automatically assesses the quality of a micro-manufactured element, such as a microchip wafer in the semiconductor industry, nanotechnology, sensor technology etc.

Having described now the preferred embodiments of this invention, it will be apparent to one of skill in the art that other embodiments incorporating its concept may be used. It is felt, therefore, that this invention should not be limited to the disclosed embodiments, but rather should be limited only by the scope of the appended claims.

The invention claimed is:

1. A reflective optical objective comprising:
   a first reflecting element having a convex or flat front surface and a back surface, wherein the entirety of the front surface of the first reflecting element is reflective such that the first reflecting element lacks a transmissive section;
   a second reflecting element having a concave reflecting surface facing the front surface of the first reflecting element, wherein the second reflecting element comprises a transmissive section permitting electromagnetic radiation to pass through the concave reflecting surface of the second reflecting element to the first reflecting element; and
   a carrier material between at least the front surface of the first reflecting element and the concave reflecting surface of the second reflecting element, wherein a dimension of the carrier material defines a distance between the first and second reflecting elements, wherein:
   the reflective optical objective has a thickness from 10 µm to 0.5 mm, a height from 50 µm to 1 mm, and a width from 50 µm to 1 mm,
   the first reflecting element is formed by inkjet-printing a first carrier-material on a substrate, thereby forming first structure having a first exposed convex surface, and depositing, by vapor deposition, a first reflective layer on the first exposed convex surface of the first structure, and
   the second reflecting element is formed by inkjet-printing a second carrier material onto the first reflecting element, thereby forming a second structure having a second exposed convex surface, and depositing, by vapor deposition, a second reflective layer on the second exposed convex surface of the second structure.

2. The reflective optical objective according to claim 1, wherein the reflective optical element further includes a carrier material embedding the back surface of the first reflecting element.

3. The reflective optical objective of claim 1, wherein the carrier material is in contact with the front surface of the first reflecting element and a front surface of the second reflecting element, the front surface of the second reflecting element including the concave reflecting surface.

4. The reflective optical objective of claim 1, wherein the carrier material is in contact with the convex reflecting surface and/or the concave reflecting surface.

5. The reflective optical objective of claim 1, wherein the transmissive section includes an aperture in the concave reflecting surface of the second reflecting element.

6. The reflective optical objective of claim 1, wherein the carrier material is a solid or partially solidified material.

7. The reflective optical objective of claim 1, wherein the reflective optical objective comprises a carrier material embedding a back surface of the second reflecting element.

8. An optical device comprising an array of reflective optical objectives according to claim 1.

9. The optical device of claim 8, comprising a plurality of micro-lens.

10. The optical device of claim 8, comprising a plurality of sensor elements for detecting reflected electromagnetic radiation, wherein each reflective optical objective is associated with a sensor element, and wherein the position of each reflective optical objective is fixed relative to an associated sensor element.

11. The optical device of claim 8, wherein the optical device is a microscope.

12. The optical device of claim 8, wherein the optical device is an endoscope or an endomicroscope.

13. A method for producing a reflective optical objective, the method comprising:
providing a substrate;
inkjet-printing a first carrier-material on the substrate, thereby forming first structure having a first exposed convex surface;
depositing, by vapor deposition, a first reflective layer on the first exposed convex surface of the first structure, thereby forming a first reflecting element having a convex reflecting surface on the first exposed convex surface of the first structure;
inkjet-printing a second carrier material onto the first reflecting element, thereby forming a second structure having a second exposed convex surface;
depositing, by vapor deposition, a second reflective layer on the second exposed convex surface of the second structure, thereby forming a second reflecting element having a concave reflecting surface on the second exposed convex surface of the second structure, wherein the second reflecting element comprises a transmissive section, wherein the reflective optical objective has a thickness from 10 µm to 0.5 mm, a height from 50 µm to 1 mm, and a width from 50 µm to 1 mm.

14. The method of claim 13, wherein the substrate comprises:
a base;
a first platform for the first reflecting element, wherein the first platform is on the base; and
a second platform for the second reflecting element, wherein the second platform is on the first platform.

15. The method of claim 14, wherein inkjet-printing the first structure comprises:
depositing, by an inkjet nozzle, a first number of drops of a material on the first platform.

16. The method of claim 15, wherein inkjet-printing the second structure comprises:
depositing, by an inkjet nozzle, a second number of drops of the material on the second platform, wherein the second number of drops is greater than the first number of drops.

17. The method of claim 13, wherein the first carrier material and the second carrier material are the same material.

18. The method of claim 17, wherein the first carrier material and the second carrier material are a photosensitive polymeric material.

* * * * *